United States Patent
Schoutens

(10) Patent No.: US 9,911,019 B2
(45) Date of Patent: Mar. 6, 2018

(54) MEDICAL DEVICE IDENTIFICATION SYSTEM

(71) Applicant: DePuy Synthes Products, Inc., Raynham, MA (US)

(72) Inventor: Robert J. Schoutens, Basel (CH)

(73) Assignee: DePuy Synthes Products, Inc., Raynham, MA (US)

( * ) Notice: Subject to any disclaimer, the term of this patent is extended or adjusted under 35 U.S.C. 154(b) by 198 days.

(21) Appl. No.: 14/950,541

(22) Filed: Nov. 24, 2015

(65) Prior Publication Data

US 2016/0148027 A1    May 26, 2016

Related U.S. Application Data

(60) Provisional application No. 62/083,996, filed on Nov. 25, 2014.

(51) Int. Cl.
| | |
|---|---|
| *G06K 7/10* | (2006.01) |
| *G06K 19/077* | (2006.01) |
| *A61B 19/00* | (2006.01) |
| *A61B 17/00* | (2006.01) |

(52) U.S. Cl.
CPC ... *G06K 7/10366* (2013.01); *G06K 19/07749* (2013.01); *A61B 2017/00526* (2013.01); *A61B 2019/448* (2013.01)

(58) Field of Classification Search
CPC ....... G06K 19/07749; G06K 19/07381; G06K 19/0739; G06K 7/10366
See application file for complete search history.

(56) References Cited

U.S. PATENT DOCUMENTS

| | | |
|---|---|---|
| 869,484 A | 10/1907 | Drake |
| 3,097,360 A | 7/1963 | Carlson et al. |
| 3,528,466 A | 9/1970 | Tracy et al. |
| 4,018,334 A | 4/1977 | Lejdegard |

(Continued)

FOREIGN PATENT DOCUMENTS

| | | |
|---|---|---|
| DE | 102011050196 | 11/2011 |
| WO | WO 2006/002667 | 1/2006 |
| WO | WO 2006/060781 | 6/2006 |

OTHER PUBLICATIONS http://www.xerafy.com/en/products.html, 2 pages, accessed Mar. 28, 2016.

(Continued)

*Primary Examiner* — Nabil Syed
(74) *Attorney, Agent, or Firm* — Baker & Hostetler LLP

(57) ABSTRACT

Instrumentation and methods of use are provided for a medical device identification system. The application describes embodiments of a system including a medical device, and an identification tag having an RFID chip and an electrical circuit. The system defines a first configuration in which a first attachment region of the electrical circuit is in electrical communication with a second attachment region of the electrical circuit, and a second configuration in which the first attachment region is electrically isolated from the second attachment region. When the system is in the first configuration the RFID chip is in a first state, and when the system is in the second configuration the RFID chip is in a second state different than the first state.

14 Claims, 14 Drawing Sheets

(56) References Cited

U.S. PATENT DOCUMENTS

| | | |
|---|---|---|
| 4,059,034 A | 11/1977 | Hornung |
| 4,112,603 A | 9/1978 | Giulie |
| 4,199,093 A | 4/1980 | Combette et al. |
| 4,577,426 A | 3/1986 | Jenkins |
| 4,856,819 A | 8/1989 | Gollon |
| 4,923,471 A | 5/1990 | Morgan |
| 4,926,719 A | 5/1990 | Kross et al. |
| 4,940,135 A | 7/1990 | Hall |
| 5,143,216 A | 9/1992 | Aurtoi et al. |
| 5,165,725 A | 11/1992 | Gollon |
| 5,424,053 A | 6/1995 | Bauer |
| 5,509,768 A | 4/1996 | Hon |
| 5,522,687 A | 6/1996 | Chen |
| 5,544,746 A | 8/1996 | Dohi |
| 5,560,657 A | 10/1996 | Morgan |
| 5,713,709 A | 2/1998 | Huang |
| 5,735,854 A | 4/1998 | Caron et al. |
| 5,735,874 A | 4/1998 | Measamer et al. |
| 5,746,742 A | 5/1998 | Runciman et al. |
| 5,913,421 A | 6/1999 | Shinjo |
| 6,295,747 B1 | 10/2001 | Francis |
| 6,328,746 B1 | 12/2001 | Gambale |
| 6,832,696 B2 | 12/2004 | Donner |
| 6,929,646 B2 | 8/2005 | Gambale |
| 7,256,699 B2 | 8/2007 | Tethrake et al. |
| 7,461,574 B2 | 12/2008 | Lewis et al. |
| 7,588,576 B2 | 9/2009 | Teague et al. |
| 7,766,920 B2 | 8/2010 | Ciccone et al. |
| 7,772,964 B2 | 8/2010 | Tethrake et al. |
| 7,785,355 B2 | 8/2010 | Mohr et al. |
| 7,789,899 B2 | 9/2010 | Markworth et al. |
| 7,794,809 B2 | 9/2010 | Plummer |
| 8,061,517 B2 | 11/2011 | Loeffler et al. |
| 8,079,518 B2 | 12/2011 | Turner et al. |
| 8,105,328 B2 | 1/2012 | Protopsaltis |
| 8,136,728 B2 | 3/2012 | Turner et al. |
| 8,167,336 B2 | 5/2012 | Minor et al. |
| 8,196,825 B2 | 6/2012 | Turner et al. |
| 8,424,420 B2 | 4/2013 | Ranta |
| 8,425,573 B2 | 4/2013 | Erickson et al. |
| 8,556,074 B2 | 10/2013 | Turner et al. |
| 8,564,416 B2 | 10/2013 | Steven et al. |
| 2002/0084904 A1* | 7/2002 | De La Huerga ........ A61J 1/035 340/573.1 |
| 2002/0188259 A1* | 12/2002 | Hickle ................... A61M 5/00 604/188 |
| 2003/0052788 A1* | 3/2003 | Kwong-Tai Chung ............... G06K 7/10346 340/573.1 |
| 2003/0127346 A1 | 7/2003 | Chen et al. |
| 2006/0006088 A1 | 1/2006 | Lin |
| 2006/0214789 A1* | 9/2006 | Posamentier ...... G06K 19/0716 340/545.6 |
| 2007/0222232 A1* | 9/2007 | Held .................... G06K 19/073 292/307 R |
| 2008/0157967 A1 | 7/2008 | Jones et al. |
| 2008/0302816 A1 | 12/2008 | Maag |
| 2009/0021345 A1 | 1/2009 | Sriharto et al. |
| 2010/0277288 A1* | 11/2010 | Cheng ................ G06K 19/0739 340/10.42 |
| 2013/0245697 A1 | 9/2013 | Hulliger |

OTHER PUBLICATIONS http://www.censis.net, Censis Tecnologies, Inc., 2003-2014, 2 pages, accessed Apr. 18, 2016.
http://www.karlstorz.com/ae/en/karl-storz-orchestrion.htm, Storz, Karl Storz—Endoskope, 4 pages accessed Apr. 18, 2016.
http://www.surgicountmedical.com/, Stryker 2014, 1 page, accessed Apr. 18, 2016.
http://rfsurg.com/products-and-technology/products, RF Surgical Systems 2014, 1 page, accessed Apr. 18, 2016.
http://www.veriteqcorp.com/, VeriTeq 2016, 2 pages, accessed Mar. 28, 2016.
www.fda.gov/MedicalDevices/DeviceRegulationandGuidance/UniqueDeviceIdentification; U.S. Department of Health and Human Sevices, U.S. Food and Drug Administration; page last updated—Jan. 7, 2016, 2 pages, accessed Apr. 18, 2016.
http://haldor-tech.com/; Haldor advanced technologies, 2 pages, accessed Apr. 18, 2016.

* cited by examiner

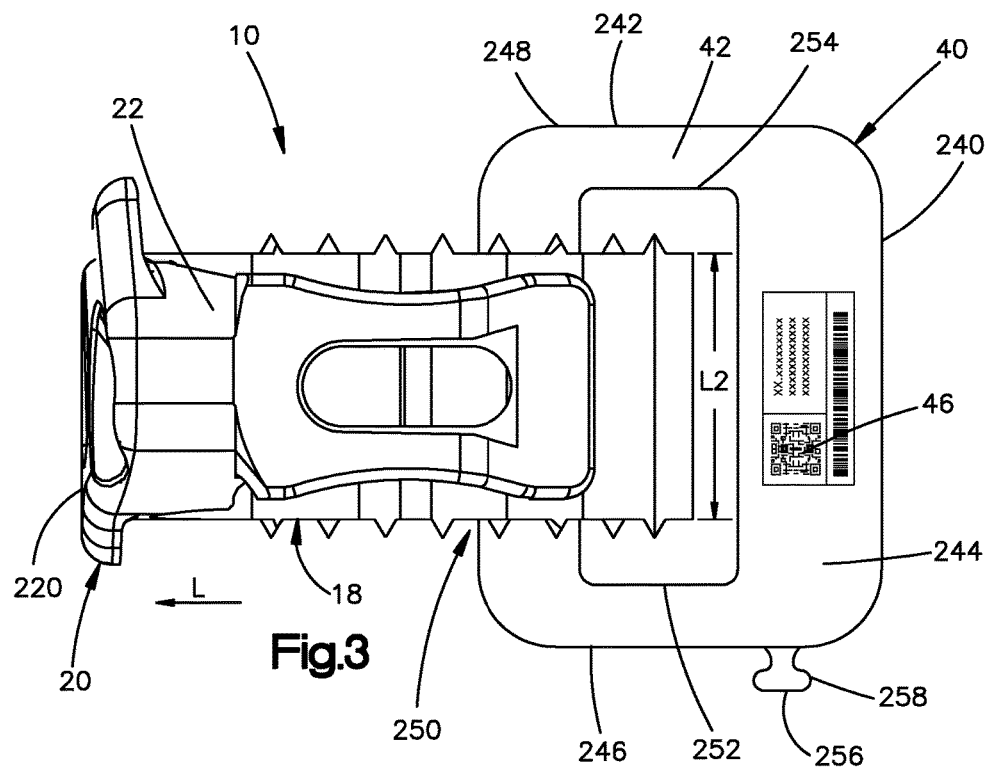
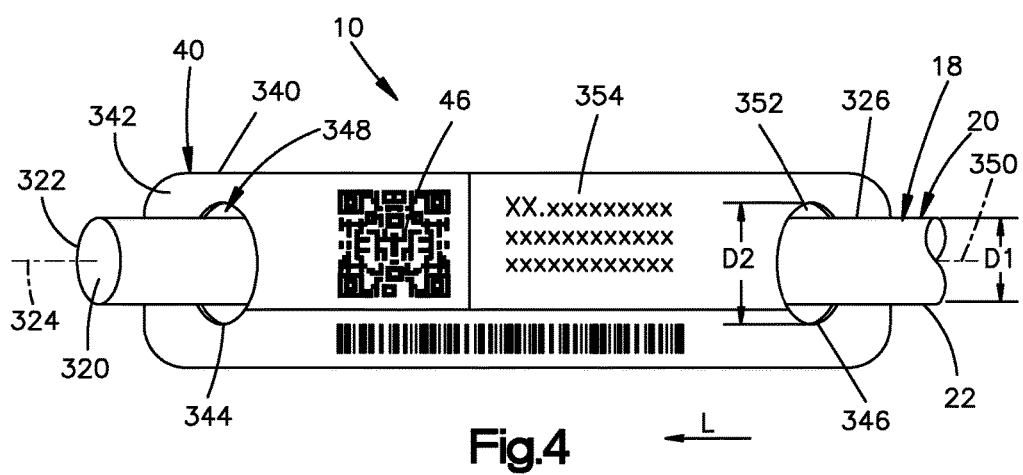

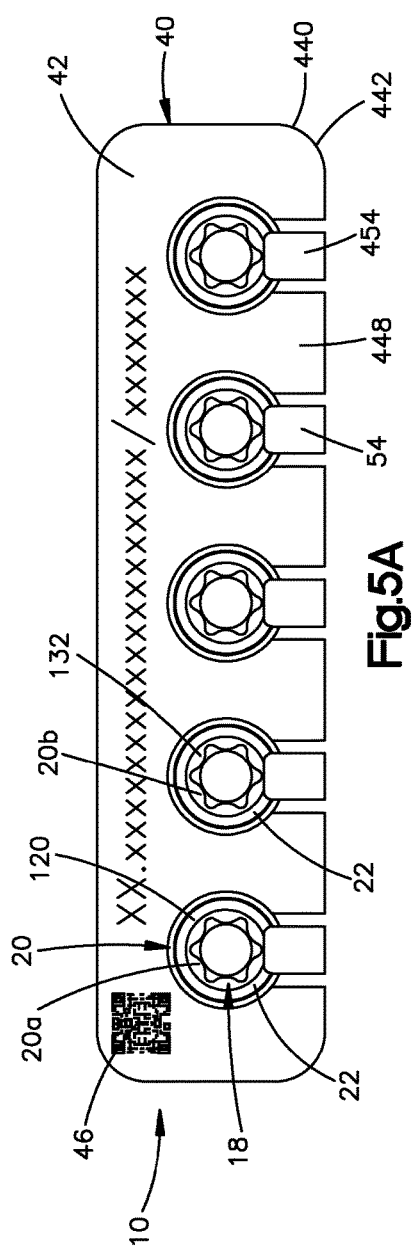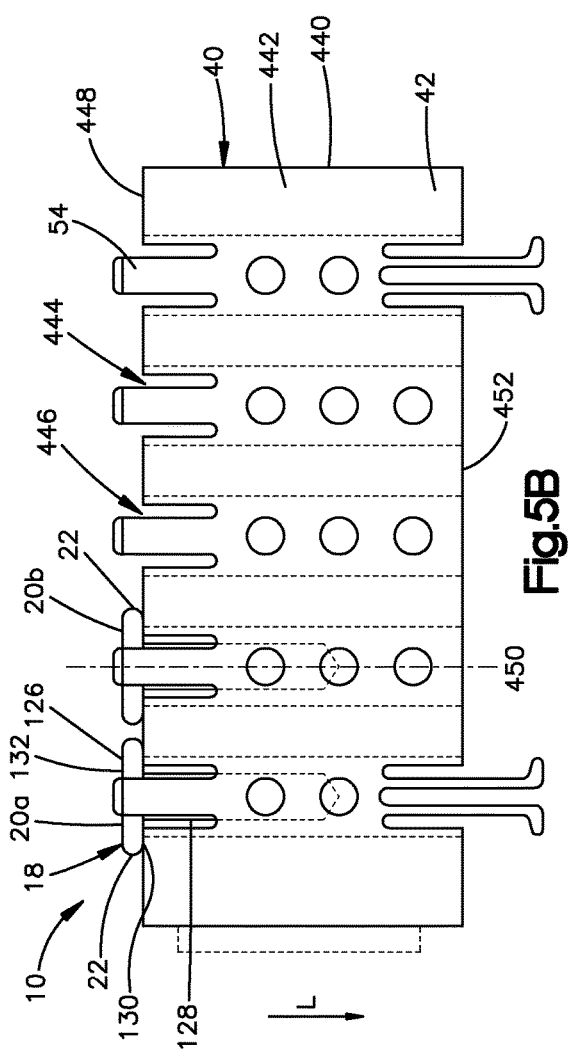

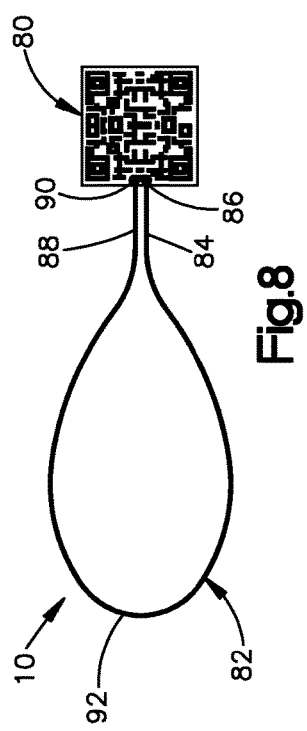
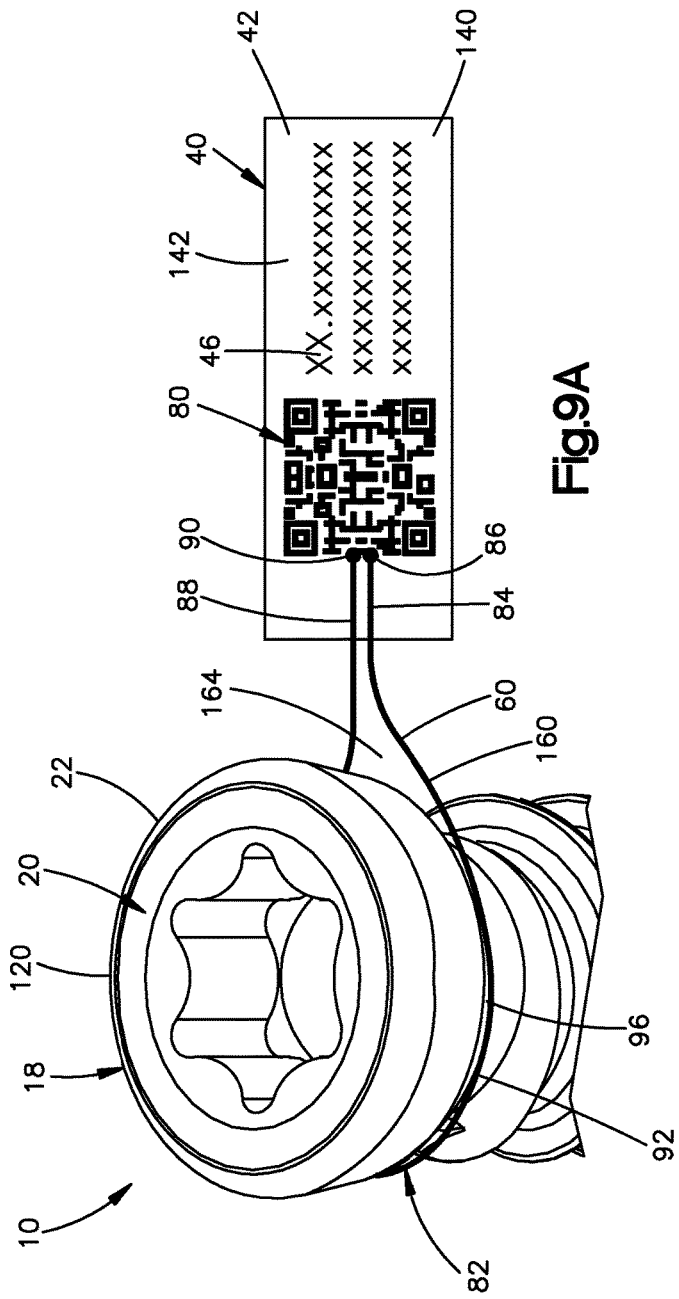

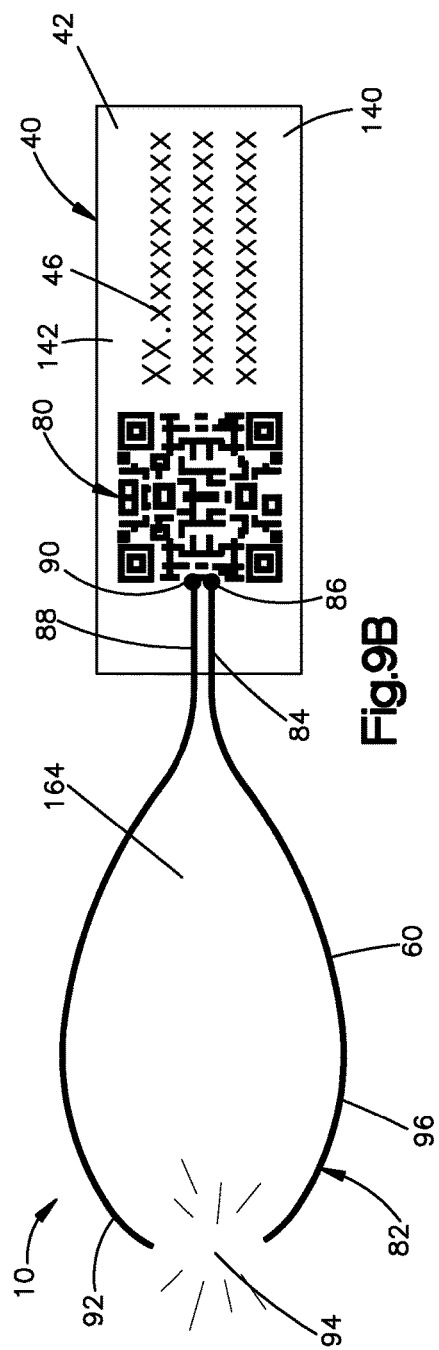

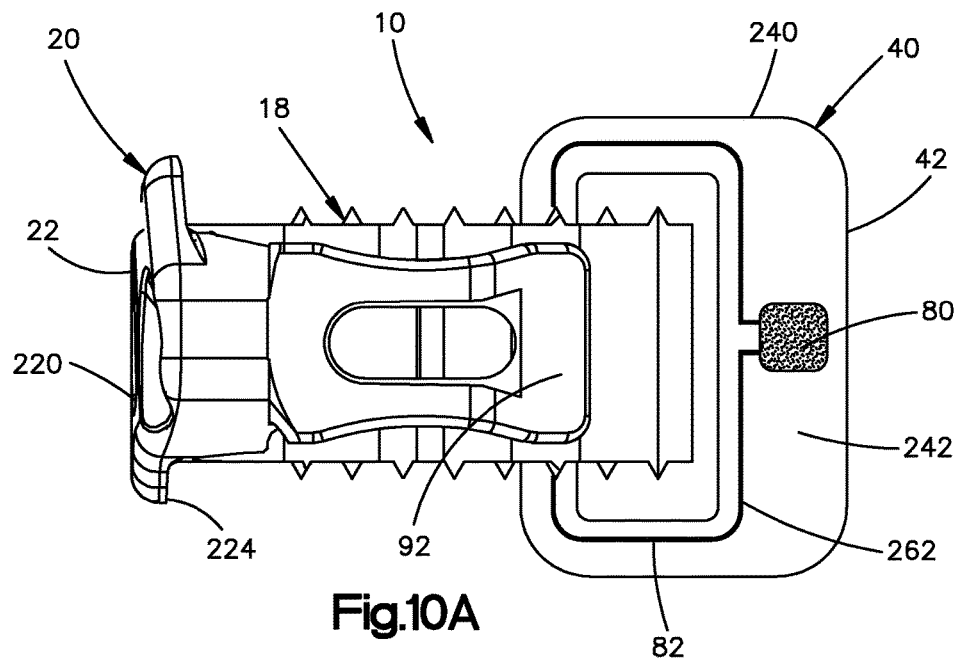
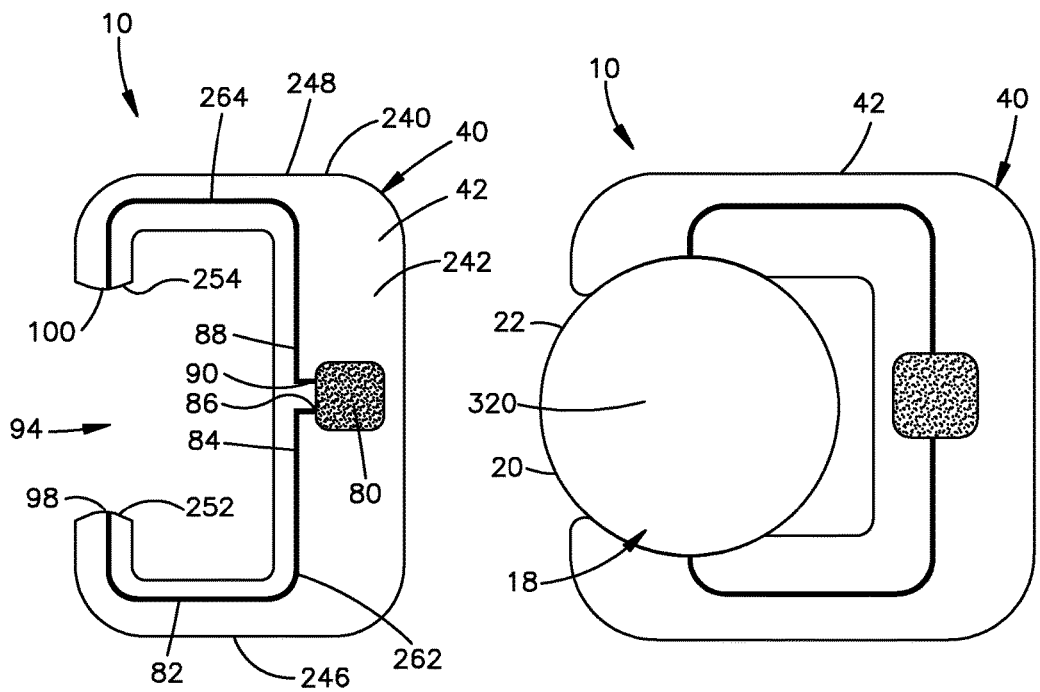
Fig.10A
Fig.10B
Fig.10C

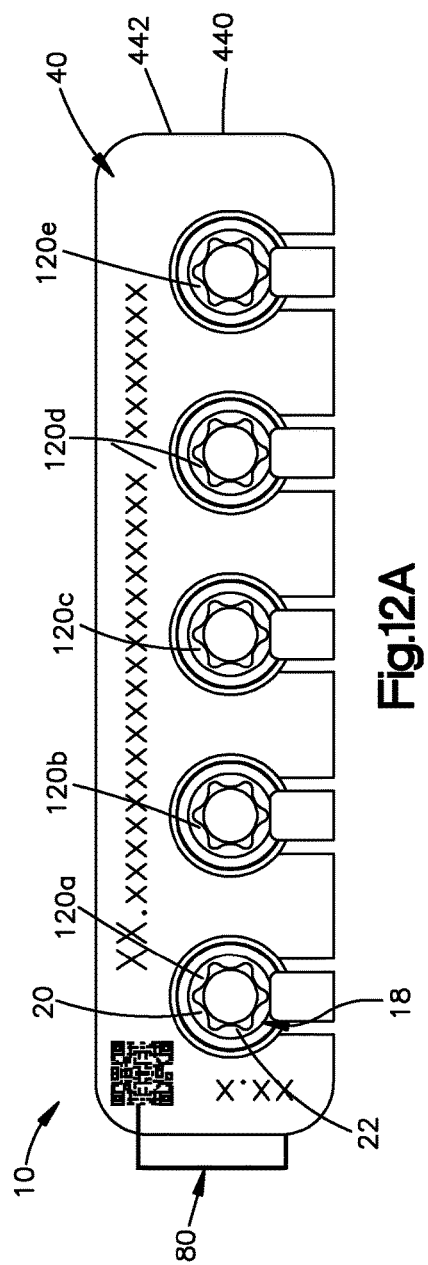
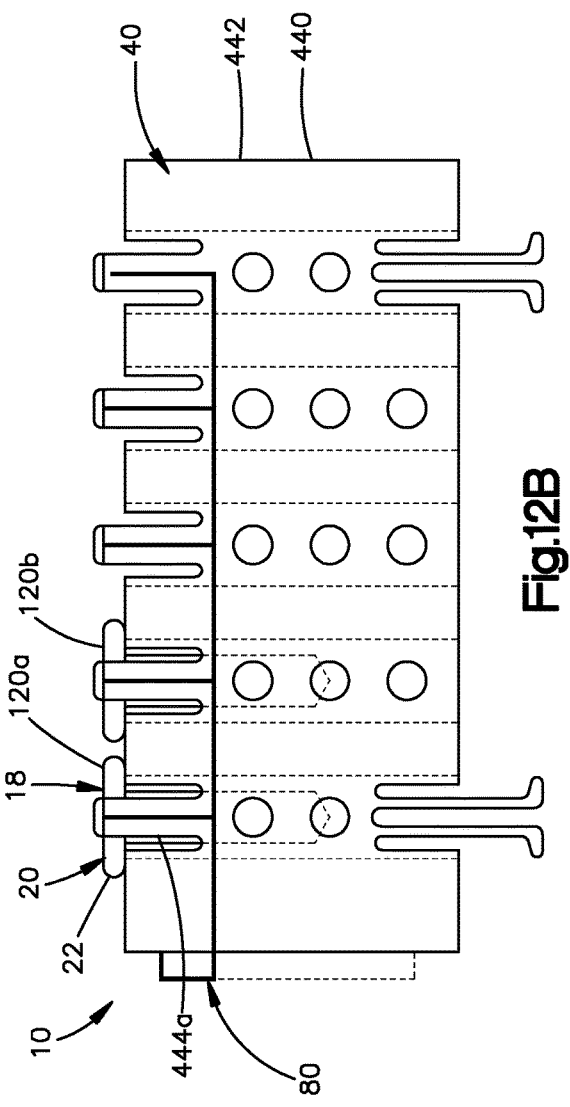
Fig.12A
Fig.12B

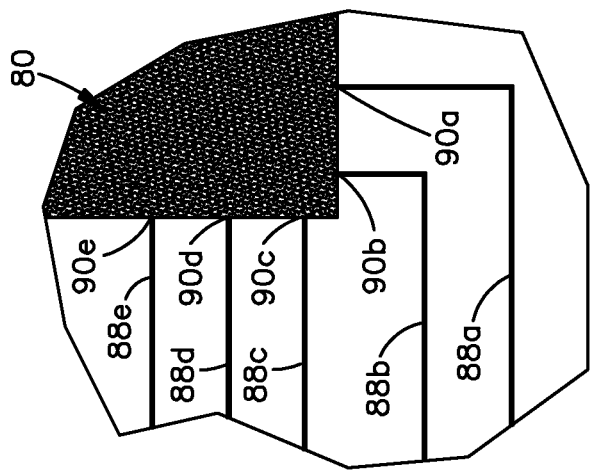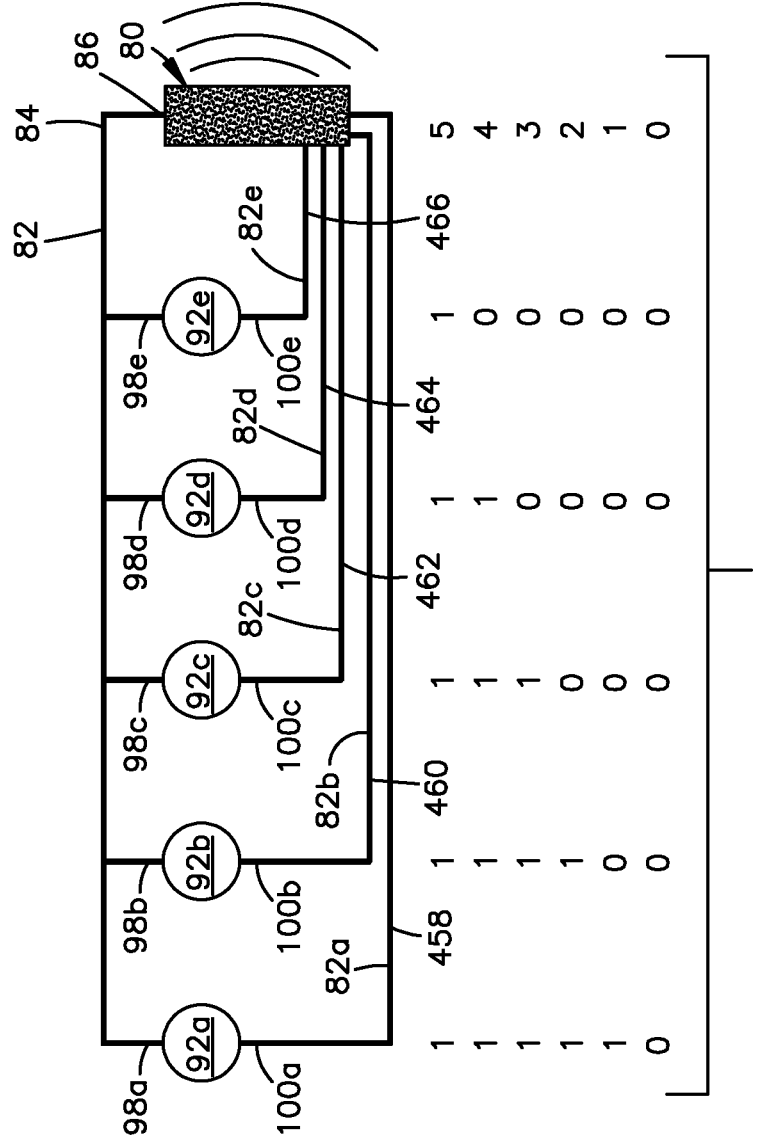

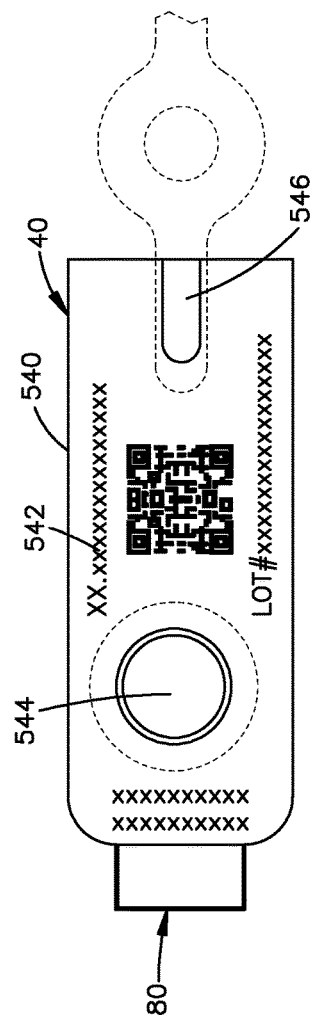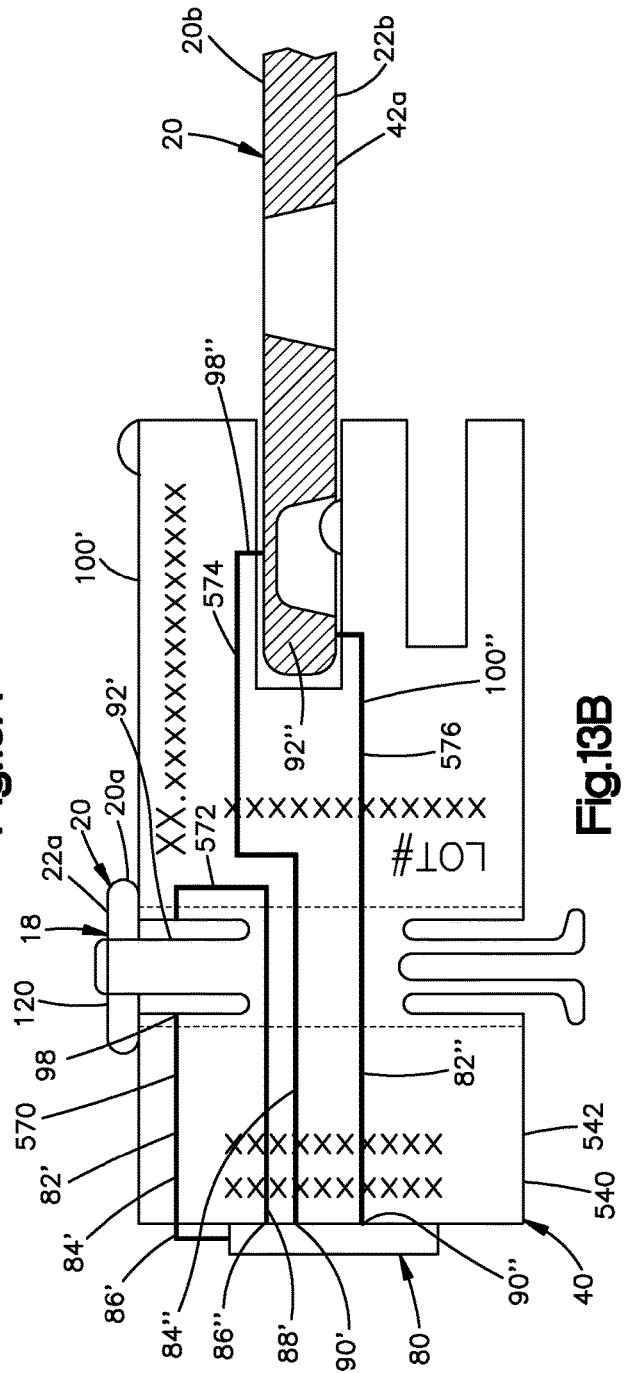

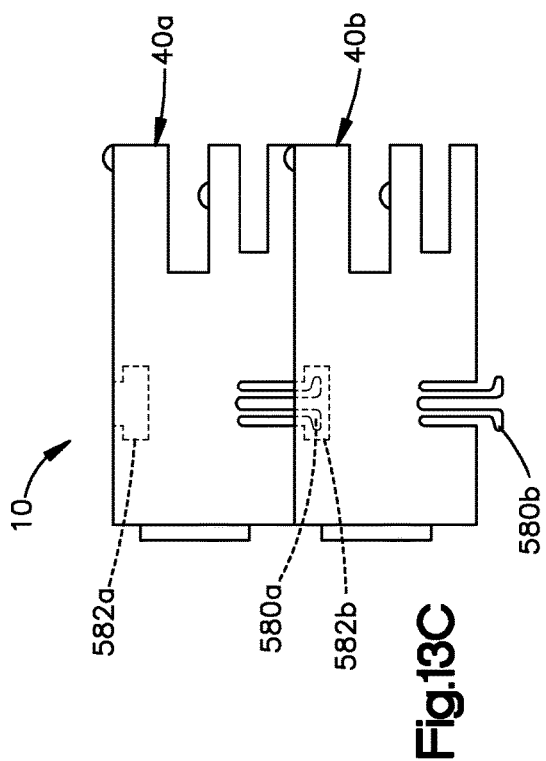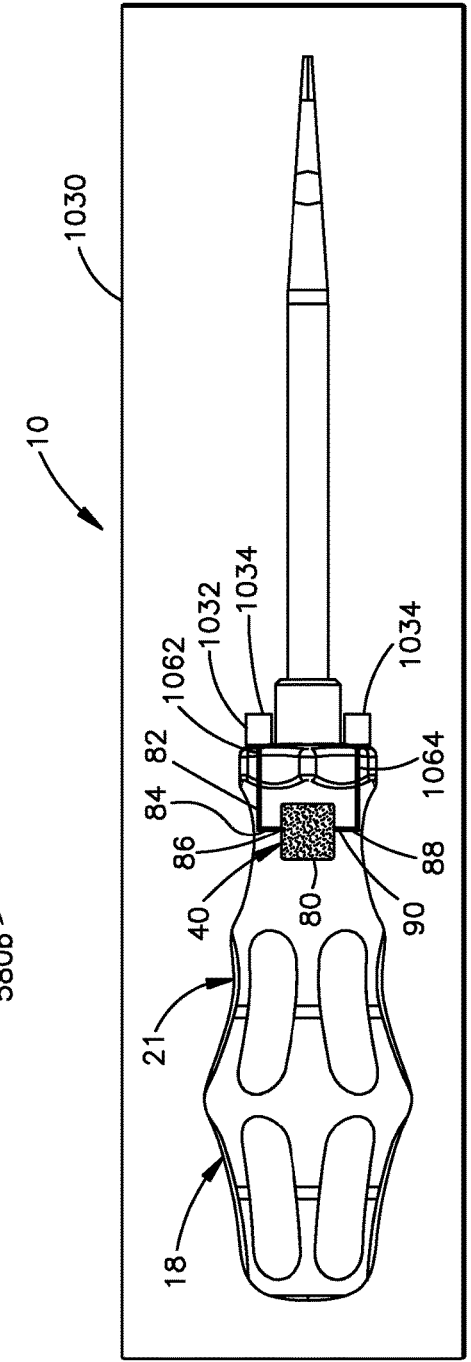

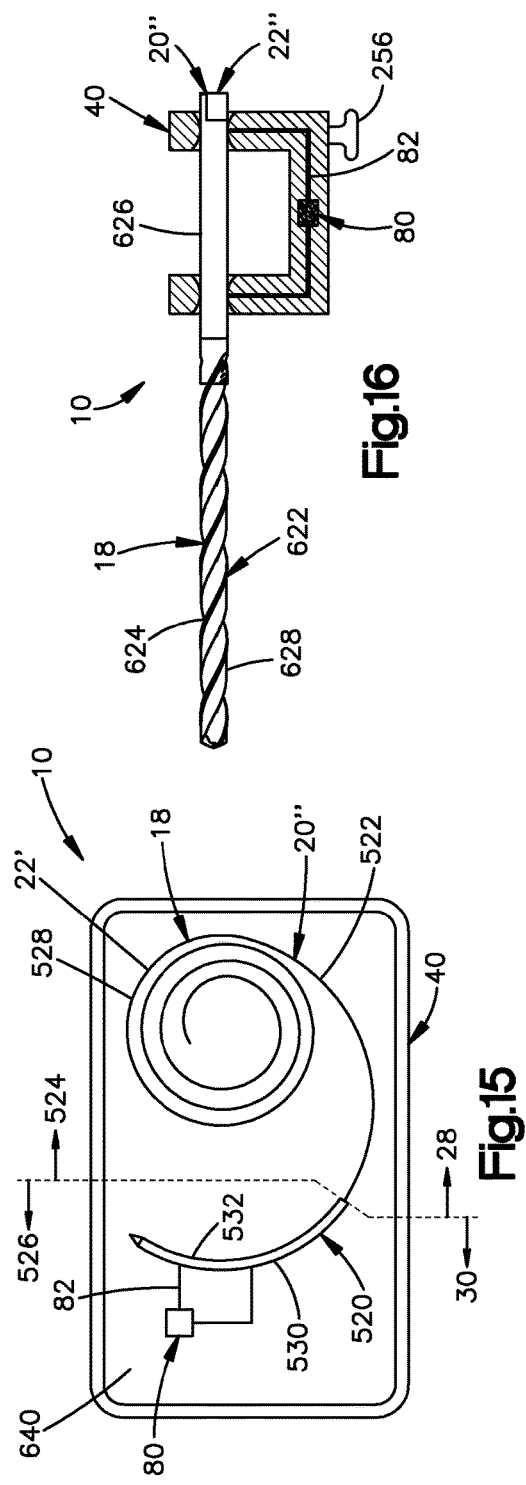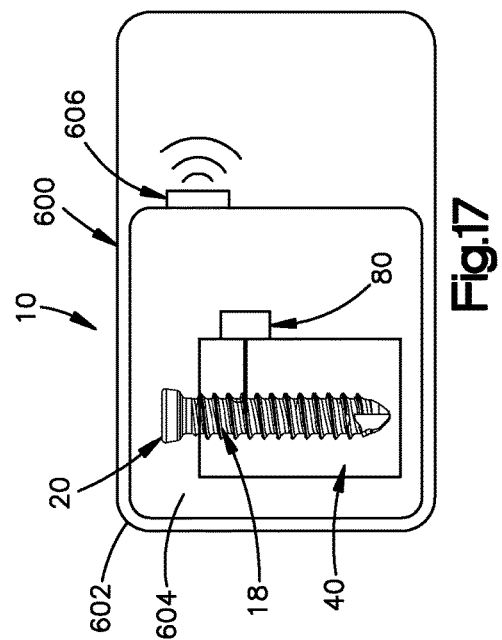

MEDICAL DEVICE IDENTIFICATION SYSTEM

CROSS REFERENCE TO RELATED APPLICATIONS

This application claims benefit of U.S. Provisional Application No. 62/083,996 filed Nov. 25, 2014, the disclosure of which is hereby incorporated by reference in its entirety.

TECHNICAL FIELD

The present application relates generally to medical devices. More specifically, the present application relates to a medical device identification system and method for the identification and tracking of medical devices, including implants and instruments.

BACKGROUND

Traditionally, many small medical devices are not identifiable once the medical device is removed from its packaging. Identification and tracking of individual medical devices, especially small medical devices that are implanted in a patient during surgery, throughout their use in the logistic chain includes several challenges. Some medical devices are too small to laser mark and in some cases laser marking a medical device may compromise the medical device rendering it unsuitable for its intended purpose. Additionally, the accompanying packaging for small medical devices may lack the space for placement of information sufficient to identify the packaged medical device.

Information regarding the time and place of manufacture, and lot or batch number of a particular medical device could allow a manufacturer of the medical device to provide updated information regarding the medical device, such as product safety notifications. Tracking the location of a medical device throughout its logistic chain can allow a manufacturer to locate a supplier, hospital, or patient that is currently in possession of the medical device. Additionally, tracking a medical device at the point of use, for example an operating room, can provide information to the manufacturer regarding when to replenish the supply of the medical device.

Accordingly, a system that tracks and provides information regarding a medical device can lead to cost savings and other improved efficiencies in the logistic chain of the medical device.

SUMMARY

The present application discloses in accordance with one embodiment a medical device identification system that includes a medical device and an identification tag coupled to the medical device. The identification tag includes an RFID chip and an electrical circuit, the electrical circuit includes a first attachment region attached to the RFID chip at a first RFID location, and a second attachment region attached to the RFID chip at a second RFID location that is spaced from the first RFID location. The system defines a first configuration in which the first attachment region is in electrical communication with the second attachment region along the electrical circuit, and a second configuration in which the first attachment region is electrically isolated from the second attachment region along the electrical circuit. The RFID chip is in a first state when the system is in the first configuration, and the RFID chip is in a second state different than the first state when the system is in the second configuration.

A method of assembling a medical device identification system is also provided including the step of coupling an identification tag to a medical device such that a first attachment region of an electrical circuit of the identification tag that is attached to an RFID chip of the identification tag at a first RFID location on the RFID chip is in electrical communication with a second attachment region of the electrical circuit of that is attached to the RFID chip at a second RFID location on the RFID chip that is spaced from the first RFID location. The method can further include the step of placing the coupled medical device and identification tag into a sterile interior of an enclosure.

A method of implanting an implant is provided including the step of selecting an implant for implantation into a patient, wherein the implant is coupled to an identification tag that includes an RFID chip and an electrical circuit, the electrical circuit having a first attachment region attached to the RFID chip at a first RFID location and a second attachment region attached to the RFID chip at a second RFID location spaced from the first RFID location, wherein the first attachment region is in electrical communication with the second attachment region along the electrical circuit, and the RFID chip is in a first state. The method can further include the step of decoupling the identification tag from the implant so as to cause a break in the electrical circuit, thereby electrically isolating the first attachment region from the second attachment region along the circuit. The method can further include the steps of in response to the decoupling step, causing the RFID chip to define a second state that is different than the first state; implanting the decoupled implant into the patient; and sensing the second state of the RFID chip.

BRIEF DESCRIPTION OF THE DRAWINGS

The foregoing summary, as well as the following detailed description of illustrative embodiments of the medical device identification system of the present application, will be better understood when read in conjunction with the appended drawings. For the purposes of illustrating the medical device identification system of the present application, there is shown in the drawings illustrative embodiments. It should be understood, however, that the application is not limited to the precise arrangements and instrumentalities shown. In the drawings:

FIG. 3 is a perspective view of a system according to another embodiment, the system including an implant and an identification tag;

FIG. 4 is a perspective view of a system according to another embodiment, the system including an implant and an identification tag;

FIG. 5A is a top plan view of a system according to another embodiment, the system including at least one implant and an identification tag;

FIG. 5B is a side elevation view of the system illustrated in FIG. 5A;

FIG. 8 is a top plan view of an identification tag including an RFID chip and an electrical circuit;

FIG. 9A is a perspective view of a system according to another embodiment, the system in a first configuration, and the system including an implant and the identification tag illustrated in FIG. 8;

FIG. 9B is a perspective view of the system illustrated in FIG. 9A, the system in a second configuration;

FIG. 9C is a cross-sectional view of a system according to another embodiment, the system in a first configuration, and the system including an implant, and system including the identification tag illustrated in FIG. 8;

FIG. 10A is a side elevation view of a system according to another embodiment, the system in a first configuration, and the system including an implant and the identification tag illustrated in FIG. 8;

FIG. 10B is a side elevation view of the system illustrated in FIG. 10A, the system in a second configuration;

FIG. 10C is a side elevation view of a system according to another embodiment, the system in a first configuration, and the system including the implant illustrated in FIG. 4 and the identification tag illustrated in FIG. 8;

FIG. 12A is a top plan view of a system according to another embodiment, the system including at least one implant, and an identification tag;

FIG. 12B is a side elevation view of the system illustrated in FIG. 12A;

FIG. 12C is a schematic view of a portion of the identification tag illustrated in FIG. 12B;

FIG. 12D is an enlarged view of the encircled portion illustrated in FIG. 12C;

FIG. 13A is a top plan view of a system according to another embodiment, the system including a first implant, a second implant, and an identification tag;

FIG. 13B is a side elevation view of the system illustrated in FIG. 13A;

FIG. 13C is a side elevation view of the system according to another embodiment, the system including first and second identification tags;

FIG. 14 is a side elevation view of a system according to another embodiment, the system including a first instrument and an identification tag;

FIG. 15 is a top plan view of a system according to another embodiment, the system including at least one implant, and an identification tag;

FIG. 16 is a side elevation view of a system according to another embodiment, the system including at least one implant, and an identification tag;

FIG. 17 is a top plan view of a system according to another embodiment, the system including an implant, an identification tag, a first package with a sterile interior, and a second package;

DETAILED DESCRIPTION OF ILLUSTRATIVE EMBODIMENTS

Figure 1:
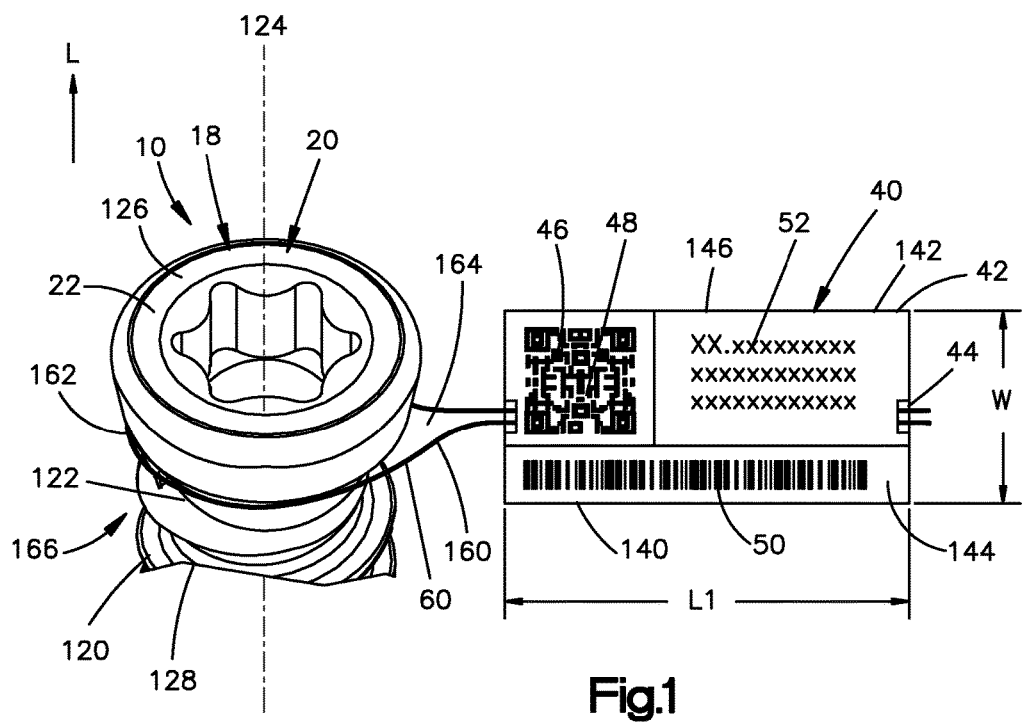
FIG. 1 is a perspective view of a system according to one embodiment, the system including an implant and an identification tag.

Certain terminology is used in the following description for convenience only and is not limiting. The term "plurality", as used herein, means more than one. The term "between" as used herein, for example "A is between B and C" means that a straight line from B to C intersects A. Reference to a structure being "between" other structures "with respect to a direction" for example "A is between B and C with respect to the longitudinal direction" means that a straight line from B to C that is parallel to the longitudinal direction intersects A. When a range of values is expressed, another embodiment includes from the one particular value and/or to the other particular value. Similarly, when values are expressed as approximations, by use of the antecedent "about," it will be understood that the particular value forms another embodiment. Further, reference to values stated in ranges includes each and every value within that range. All ranges are inclusive and combinable. Certain features of the invention which are described herein in the context of separate embodiments may also be provided in combination in a single embodiment. Conversely, various features of the invention that are described in the context of a single embodiment may also be provided separately or in any subcombination.

A three dimensional coordinate system is provided and described herein. The three dimensional coordinate system includes a longitudinal direction L, a lateral direction A that is perpendicular to the longitudinal direction L, and a transverse direction T that is perpendicular to both the longitudinal direction L and the lateral direction A.

Referring to FIGS. 1 to 7, a medical device identification system 10 (referred to herein as the system 10), includes one or more medical devices 18 and an identification tag 40. According to one embodiment, the one or more medical devices 18 may include at least one implant 20, for example an anatomical implant. According to another embodiment, the one or more medical devices 18 may include at least one instrument 21, for example an instrument configured to insert an anatomical implant. According to another embodiment, the one or more medical devices 18 may include both at least one implant 20 and at least one instrument 21. The system 10 defines a first configuration in which the medical device 18 is coupled to the identification tag 40. The system 10 may further define a second configuration in which the medical device 18 is decoupled from the identification tag 40. The identification tag 40 contains information about the medical device 18, for example the manufacture date and location, the lot and batch number, etc.

Referring to FIG. 1, the system 10, according to one embodiment, includes the medical device 18, for example an implant 20, and the system 10 further includes an identification tag 40 coupled to the implant 20 such that the system 10 is in the first configuration. The implant 20 includes an implant body 22. As shown in the illustrated embodiment, the implant body 22 can be in the form of a screw 120, for example a bone screw or a cap screw, configured to be implanted into bone. The screw 120 includes a screw body 122 that is elongate along a longitudinal axis 124 that extends in a direction, for example the longitudinal direction L. The screw body 122 includes a head 126 and a shaft 128 that extends from the head 126 along the longitudinal axis 124.

As shown in the illustrated embodiment the identification tag 40 includes a substrate 42. In one embodiment, the substrate 42 includes a card-like member 140. The card-like member 140 includes a card body 142 that defines a length L1 measured along a direction, and a width W measured along a direction perpendicular to the direction the length L1 is measured along. The card body 142 includes a first surface 144 and a second surface 146 opposite the first surface 144. Either or both of the first surface 144 and the second surface 146 can include information about the implant 20, for example the screw 120. As shown in the illustrated embodiment, identification tag 40 can include indicia 46 that contain information about the screw 120. In one embodiment, the indicia 46 are carried by the substrate 42, for example the first surface 144 of the card body 142 as shown. The indicia 46 can include a two dimensional matrix 48, such as a QR code, that stores information and is configured to be read, for example by a QR code scanner. When the two dimensional matrix 48 is read the information is transferred to the device that read the two dimensional matrix 48. In addition to, or in replacement of the two dimensional matrix 48, the indicia 46 can further include a bar code 50, and text 52.

According to one embodiment, the identification tag 40 can include an attachment member 60 that is configured to couple the identification tag 40 to the implant 20. As shown in the illustrated embodiment, the attachment member 60 includes a wire 160, for example an electrically conductive wire. In another embodiment the attachment member 60 can be a suture or other thread-like member. The attachment member 60 is configured to be secured to the identification tag 40. As shown in the illustrated embodiment, the identification tag 40 can include a recess 44. According to one embodiment, the recess 44 is defined by the substrate 42, for example the card body 142. The attachment member 60 is configured to be passed through the recess 44, thereby coupling the attachment member 60 to the identification tag 40. According to another embodiment, the identification tag 40 may be devoid of the recess 44, and the attachment member 60 is configured to be secured to the identification tag 40 through other means that do not involve the recess 44, such as an adhesive.

The attachment member 60 is further configured to be secured to the implant 20. As shown in the illustrated embodiment, when the attachment member 60 is secured to the identification tag 40, the attachment member 60 includes a loop 162, for example defined by the wire 160. As shown, the loop 162 can define a first area 164 with an outer perimeter defined by the loop 162, and a second area 166 with an inner perimeter defined by the loop 162. According to one embodiment, the attachment member 60 is configured to be secured to the implant 20 by abutting the attachment member 60 with the implant 20 such that at least a portion of the implant 20 is positioned within the first area 164.

In use, the system 10 defines a first configuration in which the identification tag 40 is coupled to the implant 20. In one embodiment, the identification tag 40 is coupled to the implant 20 when the attachment member 60 is passed through the recess 44 of the identification tag 40 and abuts the implant 20 such that at least a portion of the implant 20 is positioned within the first area 164. The system 10 further defines a second configuration in which the identification tag 40 is decoupled from the implant 20. According to one embodiment, the identification tag 40 is decoupled from the implant 20 when an entirety of the implant 20 is positioned outside the first area 164. In accordance with another embodiment, the identification tag 40 can be decoupled from the implant 20 by breaking the attachment member 60, for example severing the attachment member 60 either with a wire cutter or by hand, to remove the implant 20 from the first area 164.

Figure 2:
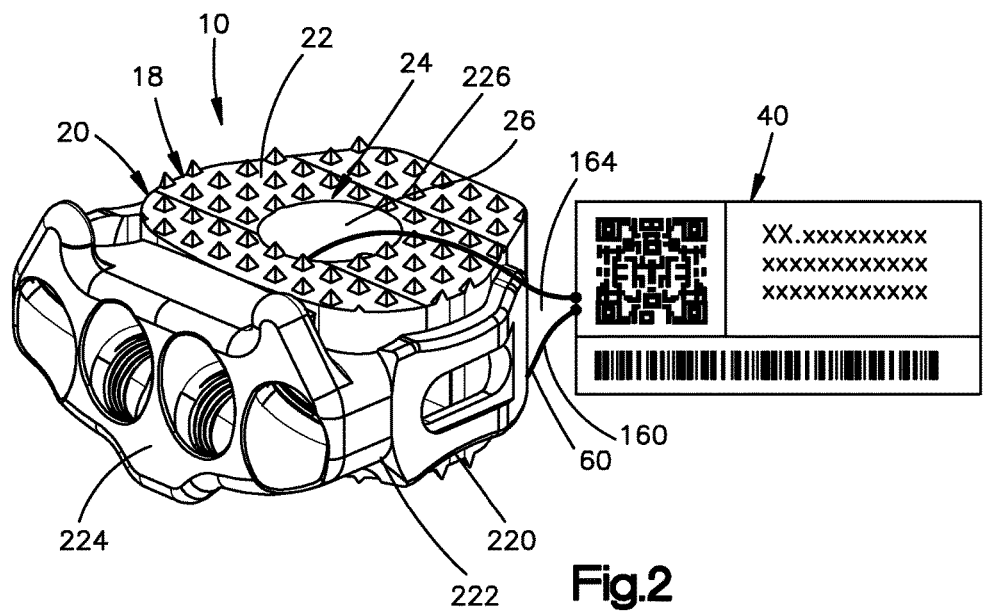
FIG. 2 is a perspective view of a system according to another embodiment, the system including an implant and an identification tag.

Referring to FIG. 2, the system 10, according to another embodiment, includes the medical device 18, for example the implant 20, and the system 10 further includes the identification tag 40 coupled to the implant 20 such that the system 10 is in the first configuration. As shown in the illustrated embodiment, the implant body 22 of the implant can be in the form of an intervertebral spacer 220 that is configured to be inserted between adjacent vertebrae. The intervertebral spacer 220 includes a spacer body 222 that has a plate 224 and a spacer 226. The implant 20 can define first and second openings 24 and a through hole 26 that extends from the first opening 24 through the implant body 22, to the second opening 24. As shown in the illustrated embodiment, the first and second openings 24 and the through hole 26 can be defined by the spacer body 222. For example the first and second openings 24 and the through hole 26 can each be defined by the plate 224 and the spacer 226 in combination. In another embodiment, the first and second openings 24 and the through hole 26 can be defined either entirely by the spacer 226 (as shown in the illustrated embodiment) or entirely by the plate 224.

The system 10, as shown, further includes the identification tag 40 as described in reference to FIG. 1. The system 10 defines a first configuration in which the identification tag 40 is coupled to the implant 20. As shown, the identification tag 40 is coupled to the implant 20 when the attachment member 60 is passed through the first and second openings 24 and the through hole 26 of the implant 20 such that at least a portion of the implant 20 is positioned within the first area 164 defined by the attachment member 60. The first area 164 can have an outer perimeter defined by the attachment member 60, for example the wire 160.

The system 10 further defines a second configuration in which the identification tag 40 is decoupled from the implant 20. According to one embodiment, the identification tag 40 is decoupled from the implant 20 when an entirety of the implant 20 is positioned outside the first area 164. In accordance with one embodiment, the identification tag 40 can be decoupled from the implant 20 by breaking the attachment member 60, for example by breaking the wire 160, to remove the wire 160 from the through hole 26 and to remove the entirety of the implant 20 from the first area 164.

Although the first and second openings 24 and the through hole 26 configured to receive the attachment member 60 are described in detail in reference to the intervertebral spacer 220 illustrated in FIG. 2, the identification tag 40 could be similarly attached to the screw 120 illustrated in FIG. 1 with the inclusion of first and second openings 24 and a through hole 26 defined by the screw body 122.

Referring to FIG. 3, the system 10, according to another embodiment, includes the medical device 18, for example the implant 20, and the system 10 further includes the identification tag 40 coupled to the implant 20 such that the system 10 is in the first configuration. As shown in the illustrated embodiment, the implant body 22 of the implant 20 is in the form of the intervertebral spacer 220 as described in detail above in reference to FIG. 2.

As shown in the illustrated embodiment, the substrate 42 of the identification tag 40 includes a spacer clamp 240. As shown in the illustrated embodiment, the spacer clamp 240 includes a clamp body 242, the clamp body 242 having a base portion 244, a first arm 246 that extends out from the base portion 244 in a direction, for example the longitudinal direction L, a second arm 248 that extends out from the base portion 244 in a direction, for example the same direction as the first arm 246, from the base portion 244. The substrate 42 can further include a gap 250 (occupied by the intervertebral spacer 220 in FIG. 3) that is configured to receive the implant 20 when the system 10 is in the first configuration. As shown in the illustrated embodiment, the gap 250 can be defined by the first arm 246 and the second arm 248. More specifically, the gap 250 can be defined by an inner surface 252 of the first arm 246 that faces the second arm 248, and can further be defined by an inner surface 254 of the second arm that faces the first arm 246.

The gap 250 defines a length L2 measured from the inner surface 252 to the inner surface 254 along a straight line in a direction, for example in a direction perpendicular to the direction the direction the first arm 246 extends out from the base portion 244. In one embodiment, the length L2 of the gap 250 is adjustable such that the length L2 can be increased to allow the implant 20 to be inserted into the gap 250. The adjustable length L2 of the gap 250 can further be decreased to couple the implant 20 to the spacer clamp 240. The adjustable length L2 of the gap 250 can also be increased to decouple the implant 20 from the spacer clamp 240 when the implant 20 is at the point of use, for example an operating room. According to another embodiment, the length L2 of the gap 250 is fixed.

According to one embodiment, the substrate 42 can be configured to be secured to a case so that the system 10 can be provided as part of a kit. Accordingly, the substrate 42 can include an engagement member 256 that is configured to secure the substrate 42 to a case. As shown in the illustrated embodiment, the engagement member 256 of the substrate 42 includes a projection 258 configured to be inserted into a corresponding recess in a case. Alternatively, the engagement member 256 of the substrate 42 can include a recess configured to receive a corresponding projection in a case. Alternatively, the substrate 42 can include a plurality of engagement members 256 or a plurality of recesses each configured to receive a corresponding projection in the case.

The spacer clamp 240 can include the indicia 46 as described above in reference to FIG. 1. The indicia 46 can be printed directly on an outer surface 260 of the clamp body 242, or alternatively the indicia 46 can be provided on a printed card member that is secured to the spacer clamp 240, for example by using an adhesive.

In use, the system 10 defines a first configuration in which the identification tag 40 is coupled to the implant 20. According to one embodiment, the identification tag 40 is coupled to the implant 20 when at least a portion of the implant 20 is positioned within the gap 250 of the spacer clamp 240. As shown, the implant 20 can abut both the first arm 246 and the second arm 248 when the system is in the first configuration. The system 10 further defines a second configuration in which the identification tag 40 is decoupled from the implant 20. According to one embodiment, the identification tag 40 is decoupled from the implant 20 when an entirety of the implant 20 is removed from the gap 250 of the spacer clamp 240, such that no portion of the implant 20 is positioned between the first arm 246 and the second arm 248.

Referring to FIG. 4, the system 10, according to another embodiment, includes the medical device 18, for example the implant 20, and the system 10 further includes the identification tag 40 coupled to the implant 20 such that the system 10 is in the first configuration. As shown in the illustrated embodiment, the implant body 22 of the implant 20 is in the form of a rod 320, for example a spinal rod configured to be implanted as part of a vertebral stabilization system. The rod 320 includes a rod body 322 that is elongate along a longitudinal axis 324 that extends in a direction, for example the longitudinal direction L. The rod body 322 includes an outer surface 326 that defines a cross-sectional dimension D1, for example a diameter, of the rod 320. As shown the cross-sectional dimension D1 can be measured along a straight line that both extends in a direction perpendicular to the longitudinal axis 324 and that passes through the longitudinal axis 324. The direction can be perpendicular to the longitudinal direction L if the longitudinal axis 324 extends along the longitudinal direction L. In one embodiment, the cross-sectional dimension D1 is measured along a straight line that lies in a plane that is normal to the longitudinal axis 324.

As shown in the illustrated embodiment the substrate 42 of the identification tag 40 includes a sleeve member 340. As shown in the illustrated embodiment, the sleeve member 340 includes a sleeve body 342, a first opening 344, a second opening 346, and a through hole 348 that extends from the first opening 344 through the sleeve body 342 to the second opening 346. The through hole 348 is configured to receive the implant 20 thereby coupling the implant 20 to the identification tag 40. The sleeve member 340 can define a sleeve axis 350 that extends through, for example centrally through, each of the first opening 344, the second opening 346, and the through hole 348. According to one embodiment, when the rod 320 is inserted into the through hole 348, the longitudinal axis 324 of the rod 320 is coincident with the sleeve axis 350.

The sleeve body 342 includes an inner surface 352 that defines a cross-sectional dimension D2, for example a diameter, of the through hole 348. As shown the cross-sectional dimension D2 can be measured in a direction perpendicular to the sleeve axis 350, and the longitudinal direction L if the sleeve axis 350 extends along the longitudinal direction L. In one embodiment, the cross-sectional dimension D2 is measured along a straight line that lies in a plane that is normal to the sleeve axis 350. According to one embodiment, the sleeve member 340 is configured such that the cross-sectional dimension D2 of the sleeve member 340 is larger than the cross-sectional dimension D1, such that the implant 20, for example the rod 320, is slidably insertable into the substrate 42, for example the through hole 348 of the sleeve member 340.

The sleeve member 340 can include the indicia 46 as described above in reference to FIG. 1. The indicia 46 can be printed directly on an outer surface 354 of the sleeve body 342, or alternatively the indicia 46 can be provided on a printed card member that is secured to the sleeve member 340.

In use, the system 10 defines a first configuration in which the identification tag 40 is coupled to the implant 20. As shown in the illustrated embodiment, the identification tag 40 is coupled to the implant 20 when the implant 20 is inserted into the through hole 348 of the sleeve member 340. The system 10 further defines a second configuration in which the identification tag 40 is decoupled from the implant 20. According to one embodiment, the identification tag 40 is decoupled from the implant 20 when an entirety of the implant 20 is removed from the through hole 348 of the sleeve member 340.

Referring to FIGS. 5A and 5B, the system 10, according to another embodiment, includes a plurality of the medical devices 18, for example a first implant 20a and a second implant 20b. According to one embodiment, the system 10 includes a plurality of implants 20, which includes the first implant 20a and the second implant 20b. According to one embodiment, the plurality of implants can include between about two of the implants 20 and about twenty of the implants 20, for example about five of the implants 20. Each of the plurality of implants 20 can be substantially identical, for example each of the plurality of implants 20 can be a screw, such as the screw 120. In another embodiment the plurality of implants 20 can include different implants, for example a bone screw and a bone plate. As shown in the illustrated embodiment, the implant body 22 of each of the plurality of implants 20 is in the form of a screw, for example the screw 120 as described in detail above in reference to FIG. 1.

The system 10 defines a first configuration in which each of the plurality of implants 20 is coupled to the identification tag 40. The system 10 defines a second configuration in which one of the plurality of implants 20 is decoupled from the identification tag 40. As shown in the illustrated embodiment the substrate 42 of the identification tag 40 includes a screw clip 440 that is configured to retain the plurality of implants 20 until each of the plurality of implants 20 is removed from the screw clip 440 for use, for example in a surgical procedure. As shown in the illustrated embodiment, the screw clip 440 includes a clip body 442 and one or more recesses 444, each of the one or more recesses 444 is configured to receive one of the implants 20. Each of the recesses 444 includes an opening 446 in a first surface 448 of the clip body 442. The recess 444 extends into the clip body 442 in a first direction, for example the longitudinal direction L, along a recess axis 450. In one embodiment the recess 444 extends through a second surface 452 of the clip body 442. As shown the second surface 452 can be opposite the first surface 448. In another embodiment the recess 444 terminates within the clip body 442 prior to reaching the second surface 452.

The screw clip 440 can include the indicia 46 as described above in reference to FIG. 1. The indicia 46 can be printed directly on the clip body 442, for example on the first surface 448. Alternatively the indicia 46 can be provided on a printed card member that is secured to the screw clip 440.

The identification tag 40 can further include an implant retention mechanism 54 configured to couple the implant 20 to the identification tag 40. As shown in the illustrated embodiment the implant retention mechanism 54 can include a resilient member 454 carried by the clip body 442. The resilient member 454 is configured to be moveable from a first position in which exit of the implant 20 out of the recess 444 is blocked, and a second position in which exit of the implant 20 out of the recess 444 is unblocked. In another embodiment the retention mechanism 54 can include internal threads formed on the clip body 442 and positioned within the recess 444. The internal threads are configured to mate with external threads of the screw 120 to couple the screw 120 to the screw clip 440.

In accordance with one embodiment, the system 10 is in the first configuration when the implant 20 is coupled to the identification tag 40. As shown, the implant 20 can be coupled to the identification tag 40 by inserting the shaft 128 of the screw 120 into the recess 444, by translating the screw 120 relative to the clip body 442 until a lower surface 130 of the head 126 abuts the first surface 448 of the clip body 442 and an upper surface 132 of the head 126 abuts the resilient member 454 with the resilient member in the first position.

In accordance with one embodiment, the system 10 is in the second configuration when the implant 20 is decoupled from the identification tag 40. When the system 10 is in the first configuration, moving the resilient member 454 from the first position to the second position allows the screw 120 to be translated relative to the clip body 442 until an entirety of the shaft 128 is removed from the recess 444.

In one embodiment, the system 10 can include a plurality of implants 20 and a plurality of recesses 444 each configured to receive one of the plurality of implants 20. For example, as shown in the illustrated embodiment, the system 10 can include five screws 120 and five recesses 444. As such the system 10 defines a first configuration in which each of the plurality of screws 120 is inserted into a respective recess 444. The system 10 defines a second configuration in which all but one of the plurality of screws 120 is inserted into a respective recess 444. The system 10 defines a third configuration in which all but two of the plurality of screws 120 are inserted into a respective recess 444. The system 10 defines a fourth configuration in which all but three of the plurality of screws 120 are inserted into a respective recess 444. The system 10 defines a fifth configuration in which all but four of the plurality of screws 120 are inserted into a respective recess 444. And the system 10 defines a sixth configuration in which none of the plurality of screws 120 are inserted into a respective recess 444. Although the illustrated embodiment shows an example of the system 10 that includes five of the screws 120, in another embodiment the system can include either more than five of the screws 120 or less than five of the screws 120.

Figure 6A:
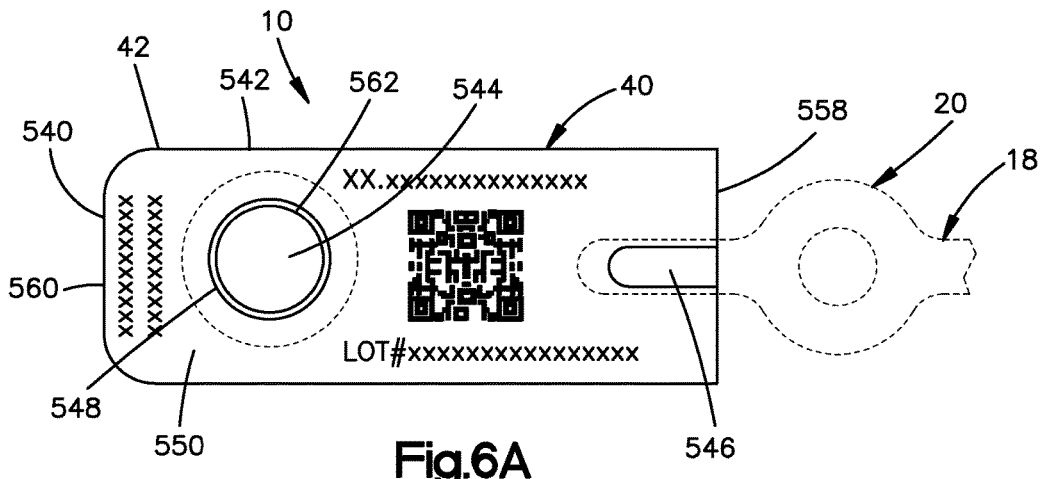
FIG. 6A is a top plan view of a system according to another embodiment, the system including a first implant, a second implant, and an identification tag.
Figure 6B:
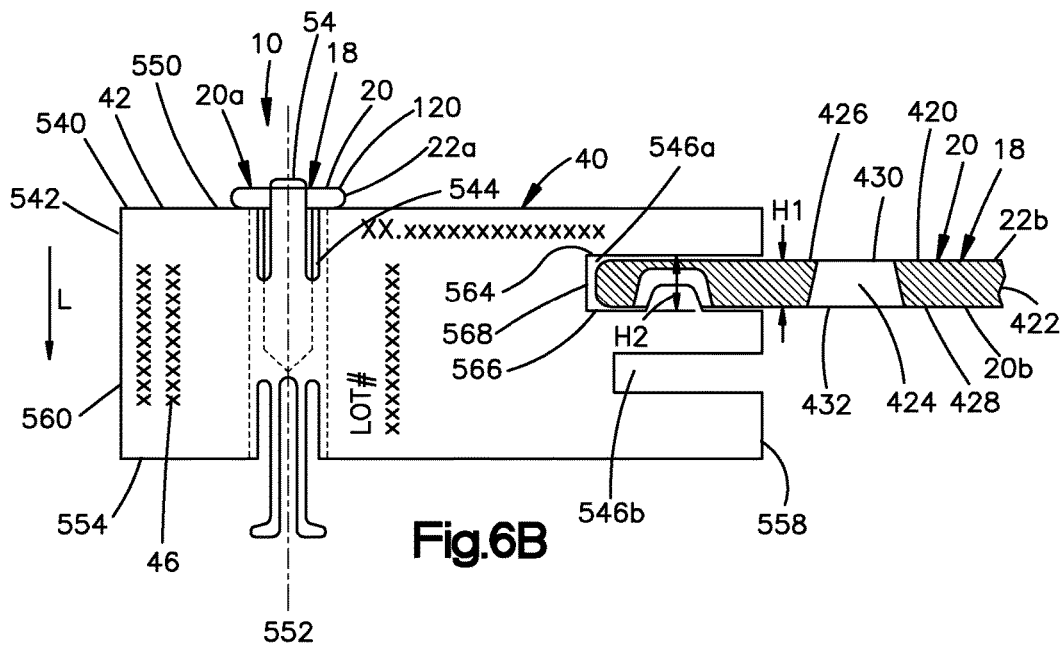
FIG. 6B is a side elevation view of the system illustrated in FIG. 6A.

Referring to FIGS. 6A and 6B, the system 10, according to another embodiment, includes a plurality of the medical devices 18, for example a plurality of the implants 20. The plurality of implants 20 can include one or more of a first implant 20a and one or more of a second implant 20b. As shown in the illustrated embodiment, the implant body 22a of the first implant 20a is in the form of a screw, for example the screw 120 as described in detail above in reference to FIG. 1. As shown in the illustrated embodiment, the implant body 22b of the second implant 20b is in the form of a bone plate 420.

According to one embodiment, the bone plate 420 includes a plate body 422 and a hole 424 that is configured to receive a fastener, such as the screw 120. The plate body 422 includes a first surface 426 and a second surface 428 opposite the first surface 426 along a direction, such as the longitudinal direction L. The bone plate 420 defines a height H1 measured from the first surface 426 to the second surface 428 along a straight line that extends in the direction. The first surface 426 defines a first opening 430 of the hole 424, and the second surface 428 defines a second opening 432 of the hole such that the hole extends through the plate body 422 from the first surface 426 to the second surface 428. The hole 424 can be one of a plurality of holes 424 defined by the bone plate 420.

As shown in the illustrated embodiment the substrate 42 of the identification tag 40 includes an implant clip 540 that is configured to retain the plurality of implants 20 until each of the plurality of implants 20 is removed from the implant clip 540 for use, for example in a surgical procedure. As shown in the illustrated embodiment, the implant clip 540 includes an implant clip body 542 a first recess 544, and a second recess 546. Each of the first recess 544 and the second recess 546 are configured to receive one of the implants 20. As shown, the first recess 544 can be configured to receive a screw, for example the screw 120 and the second recess 546 can be configured to receive a plate, for example the bone plate 420.

The first recess 544 includes a first opening 548 in a first surface 550 of the implant clip body 542. The first recess 544 extends into the implant clip body 542 in a first direction, for example the longitudinal direction L, along a recess axis 552. In one embodiment the first recess 544 extends through a second surface 554 of the implant clip body 542, the second surface 554 opposite the first surface 550. In another embodiment the first recess 544 terminates within the implant clip body 542 prior to reaching the second surface 554.

The identification tag 40 can further include the implant retention mechanism 54 (as shown in FIGS. 5A and 5B) configured to couple the implant 20 to the identification tag 40. In one embodiment the implant retention mechanism 54 can include a resilient member similar to the resilient member 454 (as shown in FIGS. 5A and 5B) carried by the implant clip body 542. In another embodiment the retention mechanism 54 can include internal threads 562 formed on the implant clip body 542 and positioned within the first recess 544. The internal threads 562 are configured to mate with external threads of the screw 120 to couple the screw 120 to the implant clip 540.

The second recess 546 includes a second opening 556 in a third surface 558 of the implant clip body 542. As shown, the third surface 558 can extend between the first surface 550 and the second surface 554, for example along the longitudinal direction. The second recess 546 extends into the implant clip body 542 in a second direction, for example in a direction either parallel to or not parallel to the longitudinal direction L. As shown in the illustrated embodiment, the second recess 546 can extend into the implant clip body 542 in a direction substantially perpendicular to the direction that the first recess 544 extends into the implant clip body 542. In one embodiment the second recess 546 extends through a fourth surface 560 of the implant clip body 542, the fourth surface 560 opposite the third surface 558. In another embodiment the second recess 546 terminates within the implant clip body 542 prior to reaching the fourth surface 560, as shown.

The implant clip body 542 can include a first inner surface 564, a second inner surface 566, and a third inner surface 568 that collectively define at least a portion, for example an entirety, of the second recess 546. As shown, the first inner surface 564 and the second inner surface 566 face one another and define a height H2 measured along a straight line that is normal to the first inner surface 564 to the second inner surface 566. The spacing between the first inner surface 564 and the second inner surface 566 can be configured such that the height H2 is slightly greater than a height of the implant 20, for example the height H1 of the bone plate 420, such that the implant 20 can be inserted into the second recess 546 to couple the implant 20 to the identification tag 40. The third inner surface 568 extends between the first inner surface 564 and the second inner surface 566 such that the third inner surface 568 defines a base or termination of the second recess 546.

The implant clip 540 can include the indicia 46 as described above in reference to FIG. 1. The indicia 46 can be printed directly on the implant clip body 542, for example on the first surface 550. Alternatively the indicia 46 can be provided on a printed card member that is secured to the implant clip 540.

In accordance with one embodiment, the system 10 defines a first configuration wherein one implant 20, for example the screw 120, is coupled to the identification tag 40 and another implant 20, for example the bone plate 420 is coupled to the identification tag 40. As shown, the system 10 is in the first configuration when the screw 120 is inserted into the first recess 544 and the bone plate 420 is inserted into the second recess 546. The system 10 further defines a second configuration wherein the first implant 20a, for example the screw 120, is decoupled from the identification tag 40 the second implant 20b, for example the bone plate 420 is coupled to the identification tag 40. For example, the system 10 is in the second configuration when an entirety of the screw 120 is removed from the first recess 544 and the bone plate 420 is inserted into the second recess 546.

The system 10 defines a third configuration wherein one implant 20, for example the screw 120, is coupled to the identification tag 40 and another implant 20, for example the bone plate 420 is decoupled from the identification tag 40. As shown, the system 10 is in the third configuration when the screw 120 is inserted into the first recess 544 and an entirety of the bone plate 420 is removed from the second recess 546. The system 10 further defines a fourth configuration wherein one implant 20, for example the screw 120, is decoupled from the identification tag 40 and another implant 20, for example the bone plate 420 is decoupled from the identification tag 40. For example, the system 10 is in the fourth configuration when an entirety of the screw 120 is removed from the first recess 544 and an entirety of the bone plate 420 is removed from the second recess 546.

In one embodiment, the system 10 includes a plurality of implants 20 and the first recess 544 is one of a plurality of first recesses 544 each configured to receive one of the plurality of implants 20. In another embodiment, the system 10 includes a plurality of implants 20 and the second recess 546 is one of a plurality of second recesses 546 each configured to receive one of the plurality of implants 20. For example, as shown in the illustrated embodiment, the implant clip 540 can include an upper second recess 546a and a lower second recess 546b, each configured to receive one of the bone plates 420.

Figure 7:
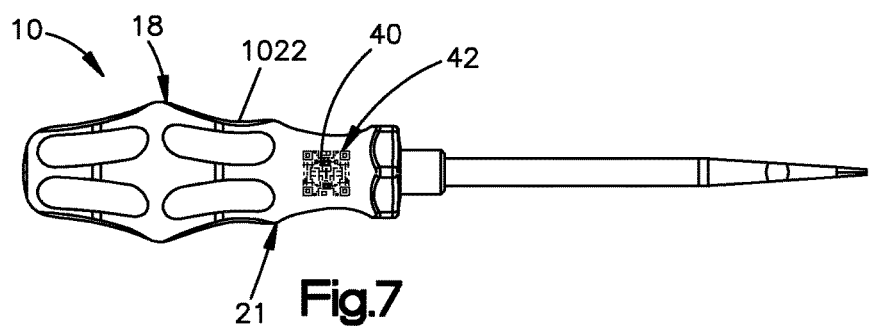
FIG. 7 is a side elevation view of a system according to another embodiment, the system including an instrument and an identification tag.

Referring to FIG. 7, the system 10, according to another embodiment, includes the medical device 18, for example the instrument 21, and the system 10 further includes the identification tag 40 coupled to the instrument 21 such that the system 10 is in the first configuration. According to one embodiment, the instrument 21 may be in the form of a screwdriver, a spinal implant inserter, any other instrument configured to use in a surgical or medical procedure, or any combination thereof.

The instrument 21 includes an instrument body 1022 that is configured to carry the identification tag 40. As shown in the illustrated embodiment, the substrate 42 is configured to be attached to the instrument body 1022. The substrate 42 can include a label. According to one embodiment the substrate 42 is configured to be attached, for example attached, to a portion of the instrument body 1022 that is configured to be gripped by a user of the instrument 21. According to another embodiment, the substrate may be configured to be attached to another portion of the instrument 21 that is not configured to be gripped by a user of the instrument 21.

According to one embodiment, the system 10 may be configured such that the identification tag 40 is permanently attached to the instrument body 1022 such that the system is devoid of a second configuration in which the medical device 18 is decoupled from the identification tag 40.

Referring to FIGS. 8, 9A, and 9B, the system 10 can include a radio-frequency identification chip 80 (referred to herein as RFID chip 80) and an electrical circuit 82. The RFID chip 80 can be turned off (or on), preventing its ability to emit (or permitting its ability to emit) a signal. The loss of the signal (or the detection of the signal) by a component of the system 10 configured to read or detect the signal, signifies that the state of the RFID chip 80 has changed. The change in state, for example, could signify that the medical device 18, for example the implant 20, has been implanted, that the implant 20 has been used (i.e. become non-sterile), or that the implant 20 requires replacement or replenishment. Alternatively, the RFID chip 80 can be configured to establish an index of states, of which it can emit its current state to a component of the system 10 for the purpose of recording the current state of the RFID chip 80.

The RFID chip 80 can include stored information about an implant 20 of the system 10. According to one embodiment the RFID chip 80 can be used as an alternative to the indicia 46 as described in reference to any of the embodiments described herein. The electrical circuit 82 can include a first attachment region 84 attached to, for example in contact with, the RFID chip 80 at a first RFID location 86, a second attachment region 88 attached to, for example in contact with, the RFID chip 80 at a second RFID location 90 that is spaced from the first RFID location 86, and an intermediate region 92 bounded by the first attachment region 84 and the second attachment region 88, the intermediate region 92 spaced from the RFID chip 80.

The electrical circuit 82 defines a closed configuration (referred to herein as the electrical circuit 82 being "closed"). According to one embodiment, the electrical circuit 82 is closed when the first attachment region 84 is in electrical communication with the second attachment region 88 along the electrical circuit 82. In accordance with another embodiment, the electrical circuit 82 is closed when the electrical circuit 82 defines an uninterrupted path from the first attachment region 84 of the electrical circuit 82, through the intermediate region 92, to the second attachment region 88 of the electrical circuit 82. For example, the path is uninterrupted, and the electrical circuit 82 is closed, when a single continuous line can be drawn from the first attachment region 84, through the intermediate region 92, to the second attachment region 88 without crossing a gap.

The electrical circuit 82 further defines an open configuration (referred to herein as the electrical circuit being "open"). According to one embodiment, the electrical circuit 82 is open when the first attachment region 84 is electrically isolated from the second attachment region 88 along the electrical circuit 82. In accordance with another embodiment, the electrical circuit 82 is open when the electrical circuit 82 defines an interrupted path from the first attachment region 84 of the electrical circuit 82, through the intermediate region 92, to the second attachment region 88 of the electrical circuit 82. For example, the path is interrupted, and the electrical circuit 82 is open, when a single continuous line cannot be drawn from the first attachment region 84, through the intermediate region 92, to the second attachment region 88 without crossing a gap.

According to one embodiment, the RFID chip 80 can include information regarding whether the electrical circuit 82 is open or closed. If the electrical circuit 82 is closed, the RFID chip 80 can define a first state. If the electrical circuit 82 is open, the RFID chip 80 can define a second state that is different than the first state.

Referring to FIGS. 9A and 9B, the system 10 can include the implant 20 and the identification tag 40 configured to be coupled to the implant 20. As shown, the implant body 22 of the implant 20 can be in the form of a screw, for example the screw 120 as described in detail in reference to FIG. 1 above. The identification tag 40 includes the substrate 42 and the attachment member 60. The substrate 42 can include the card-like member 140 and the attachment member 60 can include the wire 160 as described in detail in reference to FIG. 1 above.

The identification tag 40 includes the RFID chip 80 and the electrical circuit 82. The RFID chip 80 can be configured to be carried by the card body 142 and the electrical circuit 82 is defined by the attachment member 60, for example the wire 160, as shown in the illustrated embodiment. According to one embodiment, the wire 160 defines the first attachment region 84 of the electrical circuit 82 attached to, for example abutting, the RFID chip 80 at the first RFID location 86, the second attachment region 88 of the electrical circuit 82 attached to, for example abutting, the RFID chip 80 at the second RFID location 90, and the intermediate region 92 spaced from the RFID chip 80.

Referring to FIG. 9A, when the system 10 is in the first configuration the first attachment region 84 is in electrical communication with the second attachment region 88 along the electrical circuit 82, and the RFID chip 80 is in a first state. According to one embodiment, when the system 10 is in the first configuration the identification tag 40 is coupled to the implant 20, the electrical circuit 82 is closed, and the RFID chip 80 defines the first state. According to another embodiment, when the system 10 is in the first configuration the attachment member 60 is secured to the RFID chip 80 and the attachment member 60 abuts the implant 20 such that at least a portion of the implant 20 is positioned within the first area 164.

Referring to FIG. 9B, according to one embodiment, when the system 10 is in the second configuration the first attachment region 84 is electrically isolated from the second attachment region 88 along the electrical circuit 82, and the RFID chip 80 is in a second state different than the first state. According to another embodiment, when the system 10 is in the second configuration the identification tag 40 is decoupled from the implant 20, the electrical circuit 82 is open, and the RFID chip 80 defines a second state that is different than the first state.

As shown in the illustrated embodiment, when the system 10 is in the second configuration the identification tag 40 is decoupled from the implant 20 when an entirety of the implant 20 is positioned outside the first area 164. In accordance with another embodiment, the identification tag 40 can be decoupled from the implant 20 by breaking the attachment member 60, for example severing the attachment member 60 either with a wire cutter or by hand, to remove the implant 20 from the first area 164. As shown, decoupling the identification tag 40 from the implant 20 by breaking the attachment member 60 can open a gap 94 in the electrical circuit 82, resulting in the electrical circuit 82 being open and the RFID chip 80 defining the second state.

According to one embodiment, the identification tag 40 can include an antenna 96 configured to transmit whether the RFID chip 80 is in the first state or the second state. As shown, the antenna 96 can be at least partially, for example entirely, defined by the attachment member 60, for example the wire 160. According to another embodiment, the antenna 96 can be at least partially, for example entirely, defined by a metallic portion of the implant 20. According to another embodiment, the antenna 96 can be at least partially, for example entirely, defined by a portion of the substrate 42. According to one embodiment, when the system 10 is in the second configuration the identification tag 40 actively transmits that the RFID chip 80 is in the second state.

Referring to FIG. 9C, the system 10 can include the medical device 18, which can include the implant 20, and further include the identification tag 40 configured to be coupled to the implant 20. As shown, the identification tag 40 includes the substrate 42, the RFID chip 80, the electrical circuit 82, and the attachment member 60. According to the illustrated embodiment, the attachment member 60, can include a first wire 160*a* and a second wire 160*b*. As shown, the first wire 160*a* defines the first attachment region 84 of the electrical circuit 82 and the second wire 160*b* defines the second attachment region 88 of the electrical circuit 82.

When the system 10 is in the first configuration the first attachment region 84 is in electrical communication with the second attachment region 88 along the electrical circuit 82, and the RFID chip 80 is in a first state. According to one embodiment, when the system 10 is in the first configuration the identification tag 40 is coupled to the implant 20, the electrical circuit 82 is closed, and the RFID chip 80 defines the first state. As shown in the illustrated embodiment, when the system 10 is in the first configuration the first wire 160*a* abuts the implant 20 such that at least a portion of the implant 20 is positioned within the first area 164 and the second wire 160*b* abuts the implant 20 such that the implant 20 forms a portion of the electrical circuit 82.

When the system 10 is in the second configuration the first attachment region 84 is electrically isolated from the second attachment region 88 along the electrical circuit 82, and the RFID chip 80 is in a second state different than the first state. According to one embodiment, when the system 10 is in the second configuration the identification tag 40 is decoupled from the implant 20, the electrical circuit 82 is open, and the RFID chip 80 defines a second state that is different than the first state.

The system 10 defines the second configuration when the identification tag 40 is decoupled from the implant 20, for example when an entirety of the implant 20 is positioned outside the first area 164. In accordance with one embodiment, the system 10 can change from the first configuration to the second configuration by moving, for example translating, the implant 20 in a direction until the entirety of the implant 20 is positioned outside the first area 164 without breaking the first wire 160*a*. In accordance with another embodiment, the identification tag 40 can be decoupled from the implant 20 by breaking the first wire 160*a*, for example by severing the first wire 160*a* with a wire cutter or by hand, to remove the entirety of the implant 20 from the first area 164. Decoupling the identification tag 40 from the implant 20 by breaking the attachment member 60 can open a gap, such as the gap 94 illustrated in FIG. 9B, in the electrical circuit 82, resulting in the electrical circuit 82 being open and the RFID chip 80 defining the second state.

Referring to FIGS. 10A and 10B, the system 10 can include the medical device 18, for example the implant 20. The system 10 can further include the identification tag 40 configured to be coupled to the implant 20. As shown, the implant body 22 of the implant 20 can be in the form of a spacer, for example the intervertebral spacer 220 as described in detail in reference to FIGS. 2 and 3 above. The identification tag 40 includes the substrate 42 and the substrate 42 can include the spacer clamp 240 as described in detail in reference to FIG. 3 above.

The identification tag 40, as shown, can include the RFID chip 80 and the electrical circuit 82. The RFID chip 80 can be configured to be carried by the clamp body 242 and the electrical circuit 82 is defined partially by the identification tag 40 and partially by the implant 20. According to one embodiment, the identification tag 40 includes a first electrically conductive wire 262 (referred to herein as first wire 262) that at least partially defines the first attachment region 84 of the electrical circuit 82. As shown the first electrically conductive wire 262 can be attached directly to the RFID chip 80 at the first RFID location 86. The identification tag 40 can further include a second electrically conductive wire 264 (referred to herein as second wire 264) that defines the second attachment region 88 of the electrical circuit 82. As shown the second electrically conductive wire 264 can be attached directly to the RFID chip 80 at the second RFID location 90. The first wire 262 can be carried by the first arm 246 and the second wire 264 can be carried by the second arm 248, as shown in the illustrated embodiment.

According to another embodiment, the identification tag 40 can include a first trace that partially defines the first attachment region 84 and a second trace that partially defines the second attachment region 88. The first trace can be carried by the substrate 42 such that the first trace attaches the first electrically conductive wire 262 to the RFID chip 80 at the first RFID location 86. The second trace can be carried by the substrate 42 such that the second trace attaches the second electrically conductive wire 264 to the RFID chip 80 at the second RFID location 90.

In accordance with one embodiment, at least a portion the implant 20 can define at least a portion of the electrical circuit 82. For example a metallic portion of the intervertebral spacer 220, such as the plate 224 of the spacer body 222 (shown in FIG. 2) can define at least a portion of the intermediate region 92 of the electrical circuit 82. The electrical circuit 82 can further include a third attachment region 98 and a fourth attachment region 100 that each is attached to, for example abuts, the implant 20 when the system 10 is in the first configuration. According to one embodiment, the third attachment region 98 can be defined by the first wire 262 and positioned on the inner surface 252 of the first arm 246, and the fourth attachment region 100 can be defined by the second wire 264 and positioned on the inner surface 254 of the second arm 248, as shown.

Referring to FIG. 10A, when the system 10 is in the first configuration the identification tag 40 is coupled to the implant 20, the electrical circuit 82 is closed, and the RFID chip 80 defines the first state. According to one embodiment, the closed electrical circuit 82 defines a path that starts at the first RFID location 86 on the RFID chip 80, extends through the first wire 262 from the first attachment region 84, which is attached to the first RFID location 86, to the third attachment region 98, then extends through a portion of the implant 20, for example a metallic portion of the implant 20, such as the plate 224, that is attached to the third attachment region 98, next extends through the second wire 264 from the fourth attachment region 100, which is attached to the implant 20, to the second attachment region 88, then finally extends into the RFID chip 80 at the second RFID location 90 which abuts the second attachment region 88.

Referring to FIG. 10B, when the system 10 is in the second configuration the identification tag 40 is decoupled from the implant 20, the electrical circuit 82 is open, and the RFID chip 80 defines a second state that is different than the first state. According to one embodiment, the open electrical circuit 82 defines the gap 94 in the path that breaks electrical connectivity between the first attachment region 84 and the second attachment region 88. The gap 94 can include, for example, space devoid of a solid material (air), or a non-conductive material, such as a non-metallic material. Decoupling the implant 20 from the identification tag 40, for example removing an entirety of the intervertebral spacer 220 from between the third attachment region 98 and the fourth attachment region 100 opens the gap 94 resulting in the electrical circuit 82 being open and the system 10 being in the second configuration.

Referring to FIG. 10C, the system 10 can include the implant 20 and the identification tag 40 configured to be coupled to the implant 20. As shown, the implant body 22 of the implant 20 can be in the form of the rod 320, for example a spinal rod, which is configured to be implanted as part of a vertebral stabilization system. The identification tag 40 includes the substrate 42 and the substrate 42 includes structure similar to that of the spacer clamp 240 as described in detail in reference to FIG. 3 above.

Figure 11A:
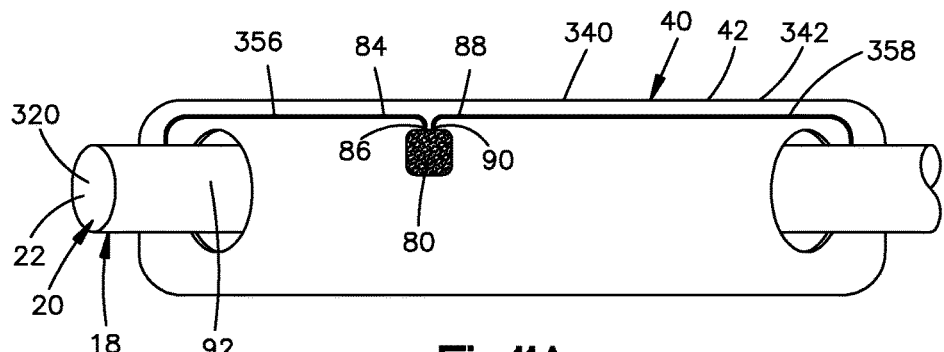
FIG. 11A a side elevation view of a system according to another embodiment, the system in a first configuration, and the system including an implant and the identification tag illustrated in FIG. 8.
Figure 11B:
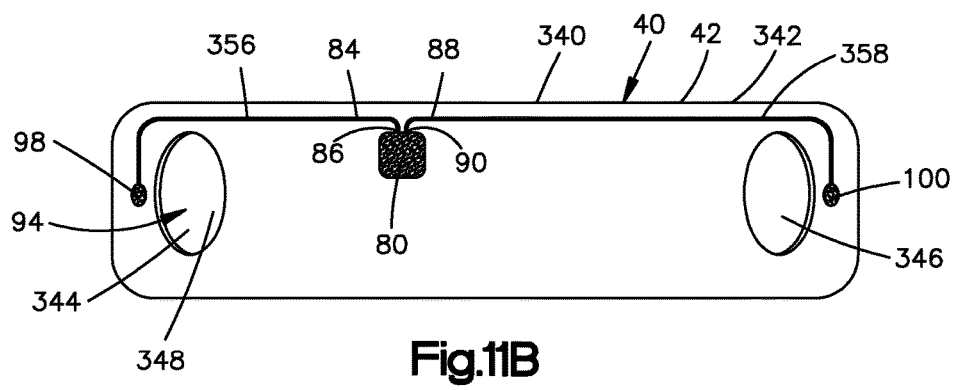
FIG. 11B is a side elevation view of the system illustrated in FIG. 11A, the system in a second configuration.
Figure 11C:
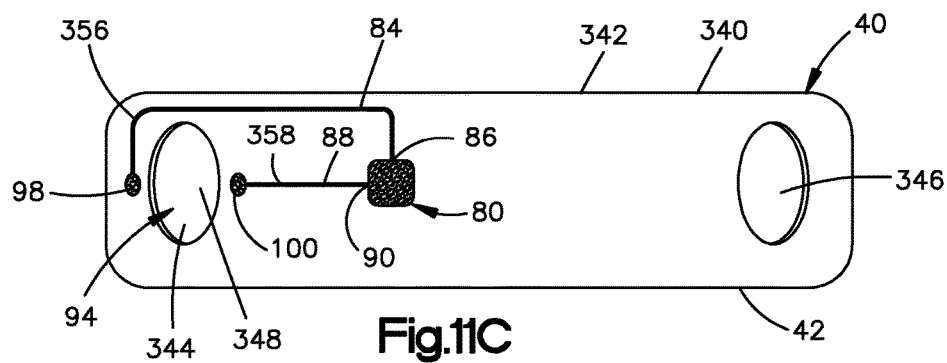
FIG. 11C is a side elevation view of the system illustrated in FIG. 11A according to another embodiment, the system in a second configuration.

Referring to FIGS. 11A to 11C, the system 10 can include the medical device 18, for example the implant 20, and the identification tag 40 configured to be coupled to the implant 20. As shown, the implant body 22 of the implant 20 can be in the form of the rod 320 as described in detail in reference to FIG. 4 above. The identification tag 40 includes the substrate 42, and the substrate 42 can include the sleeve member 340 as described in detail in reference to FIG. 4 above.

The identification tag 40, as shown, can include the RFID chip 80 and the electrical circuit 82. The RFID chip 80 can be configured to be carried by the sleeve body 342 and the electrical circuit 82 can be defined partially by the identification tag 40 and partially by the implant 20. According to one embodiment, the identification tag 40 includes a first wire 356 that defines the first attachment region 84 of the electrical circuit 82, the first attachment region 84 attached to the RFID chip 80 at the first RFID location 86. The identification tag 40 can further include a second wire 358 that defines the second attachment region 88 of the electrical circuit 82, the second attachment region 88 attached to the RFID chip 80 at the second RFID location 90. The first wire 356 and the second wire 358 can each be carried by the sleeve body 342, as shown in the illustrated embodiment.

In accordance with one embodiment, at least a portion of the implant 20 can define at least a portion of the electrical circuit 82. For example a portion of the rod 320 can define the intermediate region 92 of the electrical circuit 82, as shown in the illustrated embodiment. The electrical circuit 82 can further include a third attachment region 98 and a fourth attachment region 100 that each is attached to the implant 20 when the system 10 is in the first configuration. According to one embodiment, the third attachment region 98 can be defined by the first wire 356 and positioned proximate the first opening 344, and the fourth attachment region 100 can be defined by the second wire 358 and positioned proximate the second opening 346. According to one embodiment, each of the third attachment region 98 and the fourth attachment region 100 are positioned outside the through hole 348, as shown. In another embodiment, one or both of the third attachment region 98 and the fourth attachment region 100 could be positioned within the through hole 348.

Referring to FIG. 11A, when the system 10 is in the first configuration the identification tag 40 is coupled to the implant 20, the electrical circuit 82 is closed, and the RFID chip 80 defines the first state. According to one embodiment, the closed electrical circuit 82 defines a path that starts at the first RFID location 86 on the RFID chip 80, extends through the first wire 356 from the first attachment region 84, which is attached to the first RFID location 86, to the third attachment region 98, then extends through a portion of the implant 20, for example a metallic portion of the rod 320, that is attached to the third attachment region 98, next extends through the second wire 358 from the fourth attachment region 100, which is attached to the implant 20, to the second attachment region 88, then finally extends into the RFID chip 80 at the second RFID location 90 which is attached to the second attachment region 88.

Referring to FIG. 11B, when the system 10 is in the second configuration the identification tag 40 is decoupled from the implant 20, the electrical circuit 82 is open, and the RFID chip 80 defines a second state that is different than the first state. According to one embodiment, the open electrical circuit 82 defines the gap 94 in the path that breaks electrical connectivity between the first attachment region 84 and the second attachment region 88. The gap 94 can include, for example, space devoid of a solid material (air), or a non-conductive material, such as a non-metallic material. The gap 94 can be defined, at least in part, by the through hole 348. Decoupling the implant 20 from the identification tag 40, for example removing an entirety of the rod 320 from the between the third attachment region 98 and the fourth attachment region 100 opens the gap 94 resulting in the electrical circuit 82 being open and the system 10 being in the second configuration.

Referring to FIG. 11C, the third attachment region 98 and the fourth attachment region 100 are each positioned proximate the first opening 344. As shown, the third attachment region 98 is positioned outside the through hole 348 and the fourth attachment region 100 is positioned within the through hole 348.

Referring to FIGS. 12A to 12D, the system 10 according to another embodiment, includes the medical device 18, for example the implant 20, and the identification tag 40 configured to be coupled to the implant 20. According to one embodiment, the implant 20 is one of a plurality of implants including a first implant 20a and a second implant 20b. The plurality of implants can include between about one implant and about twenty implants, for example about five implants. In another embodiment, the plurality of implants can include more than twenty implants.

Each of the plurality of implants 20 can be substantially identical, for example each of the plurality of implants 20 can be a screw, such as the screw 120. In another embodiment the plurality of implants 20 can include different implants, for example a bone screw and a bone plate. As shown in the illustrated embodiment, the implant body 22 of each of the implants 20 is in the form of a screw, for example the screw 120 as described in detail above in reference to FIG. 1. The system 10 can further include the identification tag 40 in the form of the screw clip 440 as described in detail in reference to FIGS. 5A and 5B above.

The identification tag 40 can include the RFID chip 80 and a plurality of electrical circuits 82. The RFID chip 80 can be configured to be carried by the clip body 442 and each of the plurality of electrical circuits 82 can be defined partially by the identification tag 40 and partially by one of the plurality of implants 20. As shown in the illustrated embodiment, the identification tag 40 includes five electrical circuits 82*a*, 82*b*, 82*c*, 82*d*, and 82*e*. However, more or less electrical circuits 82 could be included in another embodiment. As shown the number of electrical circuits 82 is equal to the number of implants 20 the identification tag 40 is configured to be coupled to. However, the number of electrical circuits 82 can be different than the number of implants 20 the identification tag is configured to be coupled to in another embodiment.

According to one embodiment, each of the electrical circuits 82 includes a first attachment region 84 attached to, for example in contact with, the RFID chip 80 at a first RFID location 86, a second attachment region 88 attached to, for example in contact with, the RFID chip 80 at a second RFID location 90 that is spaced from the first RFID location 86, and an intermediate region 92 bounded by the first attachment region 84 and the second attachment region 88, the intermediate region 92 spaced from the RFID chip 80. Each of the plurality of electrical circuits 82 can be either closed or open independent of the status of the others of the plurality of electrical circuits 82.

As shown in the illustrated embodiment, the identification tag 40 includes a first wire 456 that defines the first attachment region 84 of each of the plurality of electrical circuits 82, the first attachment region 84 attached to the RFID chip 80 at the first RFID location 86. In another embodiment, each of the plurality of electrical circuits 82 can include their own individual wire that defines separate first attachment regions 84 for each of the plurality of electrical circuits 82. The identification tag 40 can further include a second wire 458 that defines the second attachment region 88*a* of the first electrical circuit 82*a* which is attached to the RFID chip 80 at the second RFID location 90*a*.

The identification tag 40 can further include a third electrically conductive wire 460 (referred to herein as third wire 460) that defines the second attachment region 88*b* of the second electrical circuit 82*b* which is attached to the RFID chip 80 at the second RFID location 90*b*. The identification tag 40 can further include a fourth electrically conductive wire 462 (referred to herein as fourth wire 462) that defines the second attachment region 88*c* of the third electrical circuit 82*c* which is attached to the RFID chip 80 at the second RFID location 90*c*. The identification tag 40 can further include a fifth electrically conductive wire 464 (referred to herein as fifth wire 464) that defines the second attachment region 88*b* of the fourth electrical circuit 82*d* which is attached to the RFID chip 80 at the second RFID location 90*d*. The identification tag 40 can further include a sixth electrically conductive wire 466 (referred to herein as sixth wire 466) that defines the second attachment region 88*e* of the fifth electrical circuit 82*e* which is attached to the RFID chip 80 at the second RFID location 90*e*. As shown in the illustrated embodiment, each of the first wire 456, the second wire and the second wire 458, the third wire 460, the fourth wire 462, the fifth wire 464, and the sixth wire 466 can each be carried by the clip body 442.

In accordance with one embodiment, at least a portion each of the plurality of implants 20 can define at least a portion of one of the plurality of electrical circuits 82. For example a portion of the first screw 120*a* can define the intermediate region 92*a* of the first electrical circuit 82*a*, as shown in the illustrated embodiment. The first electrical circuit 82*a* can further include a third attachment region 98*a* and a fourth attachment region 100*a* that each is attached to the first implant 20*a* when the system 10 is in the first configuration. According to one embodiment, the third attachment region 98*a* can be defined by the first wire 456 and positioned the first recess 444*a*, and the fourth attachment region 100*a* can be defined by the second wire 458 and positioned proximate the first recess 444*a*. The third attachment region 98*a* and the fourth attachment region 100*a* are positioned such that when the first screw 120*a* is positioned within the first recess 444*a*, both the third attachment region 98*a* and the fourth attachment region 100*a* attach to the first screw 120*a*. The others of the plurality of electrical circuits 82, for example the second electrical circuit 82*b*, the third electrical circuit 82*c*, etc., can include respective third and fourth attachment regions 98*b*, 98*c*, etc. and 100*b*, 100*c*, etc. as described in reference to the first electrical circuit 82*a* above, such that a second screw 120*b* defines a portion of the second electrical circuit 82*b*, and a third screw 120*c* defines a portion of the third electrical circuit 82*c*.

The system 10, according to one embodiment, defines a first configuration in which each of the plurality of screws 120 is coupled to the identification tag 40, each of the plurality of electrical circuits 82 is closed, and the RFID chip 80 defines a first state. The system 10 can further define a second configuration in which all but one of the plurality of screws 120 is coupled to the identification tag 40, all but one of the plurality of electrical circuits 82 is closed, and the RFID chip 80 defines a second state different than the first state. In other words, in the second configuration one of the plurality of screws 120 is decoupled from the identification tag 40 and one of the plurality of electrical circuits 82 is open. The system 10 can further define a third configuration in which all but two of the plurality of screws 120 is coupled to the identification tag 40, all but two of the plurality of electrical circuits 82 is closed, and the RFID chip 80 defines a third state different from both the first state and the second state. The system 10 can further define a fourth configuration in which all but three of the plurality of screws 120 is coupled to the identification tag 40, all but three of the plurality of electrical circuits 82 is closed, and the RFID chip 80 defines a fourth state different from each of the first state, the second state, and the third state.

The system 10 can further define a fifth configuration in which one of the plurality of screws 120 is decoupled from the identification tag 40, one of the plurality of electrical circuits 82 is open, and the RFID chip 80 defines a fifth state different from each of the first state, the second state, the third state, and the fourth state. The system 10 can further define a sixth configuration in which each of the plurality of screws 120 is decoupled from the identification tag 40, each of the plurality of electrical circuits 82 is open, and the RFID chip 80 defines a sixth state different from each of the first state, the second state, the third state, the fourth state, and the fifth state. Each of the first state, the second state, the third state, the fourth state, the fifth state, and the sixth state can correspond to a number of the screws 120 that remain coupled to the identification tag 40.

According to one embodiment the first state corresponds to the identification tag 40 being full, or including five screws. The second state can correspond to the identification tag 40 missing one screw, or including four screws. The third state can correspond to the identification tag 40 missing two screws, or including three screws. The fourth state can correspond to the identification tag 40 missing three screws, or including two screws. The fifth state can correspond to the identification tag 40 missing four screws, or including one screw. The sixth state can correspond to the identification tag 40 missing all of the screws, or including zero screws.

Although the illustrated embodiment shows an example of the system 10 that includes five of the screws 120, in another embodiment the system can include either more than five of the screws 120 or less than five of the screws 120.

Referring to FIGS. 13A and 13B, the system 10 according to another embodiment, includes a plurality of the medical devices 18, for example a plurality of the implants 20, and an identification tag 40. The plurality of implants 20 including one or more of a first implant 20*a* and one or more of a second implant 20*b*. As shown in the illustrated embodiment, the implant body 22*a* of each of the first implants 20*a* is in the form of a screw, for example the screw 120 as described in detail above in reference to FIG. 1. As shown in the illustrated embodiment, the implant body 22*b* of each of the second implants 20*b* is in the form of a plate, for example the bone plate 420 as described in detail above in reference to FIGS. 6A and 6B. As shown in the illustrated embodiment, the identification tag 40 includes the implant clip 540 as described in detail above in reference to FIGS. 6A and 6B.

Each of the first implants 20*a* can be substantially identical, for example each of the first implants 20*a* can be a screw, such as the screw 120. In another embodiment the first implants 20*a* can include different implants, for example locking bone screws and non-locking bone screws. Each of the second implants 20*b* can be substantially identical, for example each of the second implants 20*b* can be a locking bone plate. In another embodiment the second implants 20*b* can include different implants, for example locking bone plates and non-locking bone plates.

The identification tag 40 can include the RFID chip 80 and at least one electrical circuit 82. The RFID chip 80 can be configured to be carried by the implant clip body 542. The at least one electrical circuit 82 can include a first set of electrical circuits 82' and a second set of electrical circuits 82". The first set of electrical circuits 82' can include a single electrical circuit or a plurality of electrical circuits. The second set of electrical circuits 82" can also include a single electrical circuit or a plurality of electrical circuits.

Each of the first set of electrical circuits 82' can be defined partially by the identification tag 40 and partially by one of the first implants 20*a*. According to one embodiment, each of the first set of electrical circuits 82' includes a first attachment region 84' attached to the RFID chip 80 at a first RFID location 86', a second attachment region 88' attached to the RFID chip 80 at a second RFID location 90' that is spaced from the first RFID location 86', and an intermediate region 92' bounded by the first attachment region 84' and the second attachment region 88', the intermediate region 92' spaced from the RFID chip 80. Each of the first set of electrical circuits 82' can be either closed or open independent of the status of the others of the first set of electrical circuits 82'.

As shown in the illustrated embodiment, the identification tag 40 includes a first wire 570 that defines the first attachment region 84' of one of the first set of electrical circuits 82', the first attachment region 84' attached to the RFID chip 80 at the first RFID location 86'. The identification tag 40 can further include a second wire 572 that defines the second attachment region 88' of the one of the first set of electrical circuits 82' which is attached to the RFID chip 80 at the second RFID location 90'.

In accordance with one embodiment, at least a portion of one of the first implants 20*a* can define at least a portion of the one of the first set of electrical circuits 82'. For example a portion of the screw 120 can define the intermediate region 92' of the one of the first set of electrical circuit 82', as shown in the illustrated embodiment. The one of the first set of electrical circuits 82' can further include a third attachment region 98' and a fourth attachment region 100' that each is attached to the screw 120 when the system 10 is in the first configuration. According to one embodiment, the third attachment region 98' can be defined by the first wire 570 and positioned proximate the first recess 544, and the fourth attachment region 100' can be defined by the second wire 572 and positioned proximate the first recess 544. The third attachment region 98' and the fourth attachment region 100' can be positioned such that when the screw 120 is positioned within the first recess 544, both the third attachment region 98' and the fourth attachment region 100' are attached to the screw 120. According to one embodiment, the first set of electrical circuits 82' can include a plurality of electrical circuits 82' similar to the one of the first set of electrical circuits 82' as described above.

Each of the second set of electrical circuits 82" can be defined partially by the identification tag 40 and partially by one of the second implants 20*b*. According to one embodiment, each of the second set of electrical circuits 82" includes a first attachment region 84" attached to, for example in contact with, the RFID chip 80 at a first RFID location 86", a second attachment region 88" attached to, for example in contact with, the RFID chip 80 at a second RFID location 90" that is spaced from the first RFID location 86", and an intermediate region 92" bounded by the first attachment region 84" and the second attachment region 88", the intermediate region 92" spaced from the RFID chip 80. Each of the second set of electrical circuits 82" can be either closed or open independent of the status of the others of the second set of electrical circuits 82".

As shown in the illustrated embodiment, the identification tag 40 includes a third electrically conductive wire 574 (referred to herein as third wire 574) that defines the first attachment region 84" of one of the second set of electrical circuits 82", the first attachment region 84" attached to the RFID chip 80 at the first RFID location 86". The identification tag 40 can further include a fourth electrically conductive wire 576 (referred to herein as fourth wire 576) that defines the second attachment region 88" of the one of the second set of electrical circuits 82" which is attached to the RFID chip 80 at the second RFID location 90".

In accordance with one embodiment, at least a portion of one of the second implants 20*b* can define at least a portion of the one of the second set of electrical circuits 82". For example a portion of the bone plate 420 can define the intermediate region 92" of the one of the second set of electrical circuits 82", as shown in the illustrated embodiment. The one of the second set of electrical circuits 82" can further include a third attachment region 98" and a fourth attachment region 100" that each attach to the bone plate 420 when the system 10 is in the first configuration. According to one embodiment, the third attachment region 98" can be defined by the third wire 574 and positioned proximate the second recess 546, and the fourth attachment region 100" can be defined by the fourth wire 576 and positioned proximate the second recess 546. The third attachment region 98" and the fourth attachment region 100" can be positioned such that when the bone plate 420 is positioned within the second recess 546, both the third attachment region 98" and the fourth attachment region 100" attach to the bone plate 420. According to one embodiment, the second set of electrical circuits 82" can include a plurality of electrical circuits 82" similar to the one of the second set of electrical circuits 82" as described above.

In accordance with one embodiment, the system 10 defines a first configuration wherein the first implant 20*a*, for example the screw 120, is coupled to the identification tag 40, the second implant 20*b*, for example the bone plate 420 is coupled to the identification tag 40, the one of the first set of electrical circuits 82' is closed, the one of the second set of electrical circuits 82" is closed, and the RFID chip 80 defines a first state. As shown, the system 10 is in the first configuration when the screw 120 is inserted into the first recess 544 and the bone plate 420 is inserted into the second recess 546.

In accordance with one embodiment, the system 10 can define a second configuration wherein the first implant 20*a*, for example the screw 120, is decoupled from the identification tag 40, the second implant 20*b*, for example the bone plate 420 is coupled to the identification tag 40, the one of the first set of electrical circuits 82' is open, the one of the second set of electrical circuits 82" is closed, and the RFID chip 80 defines a second state that is different than the first state. As shown, the system 10 is in the second configuration when an entirety of the screw 120 is removed from the first recess 544 and the bone plate 420 is inserted into the second recess 546.

In accordance with one embodiment, the system 10 can define a third configuration wherein the first implant 20*a*, for example the screw 120, is coupled to the identification tag 40, the second implant 20*b*, for example the bone plate 420 is decoupled from the identification tag 40, the one of the first set of electrical circuits 82' is closed, the one of the second set of electrical circuits 82" is open, and the RFID chip 80 defines a third state that is different than both the first state and the second state. As shown, the system 10 is in the third configuration when at least a portion of the screw 120 is inserted into the first recess 544 and an entirety of the bone plate 420 is removed from the second recess 546.

In accordance with one embodiment, the system 10 can define a fourth configuration wherein the first implant 20*a*, for example the screw 120, is decoupled from the identification tag 40, the second implant 20*b*, for example the bone plate 420 is decoupled from the identification tag 40, the one of the first set of electrical circuits 82' is open, the one of the second set of electrical circuits 82" is open, and the RFID chip 80 defines a fourth state that is different than each of the first state, the second state, and the third state. As shown, the system 10 is in the fourth configuration when an entirety of the screw 120 is removed from the first recess 544 and an entirety of the bone plate 420 is removed from the second recess 546.

Referring to FIG. 13C, the system 10 according to another embodiment, includes a plurality of identification tags 40, including a first identification tag 40*a* and a second identification tag 40*b*. According to one embodiment, the first identification tag 40*a* and the second identification tag 40*b* can each be in the form of the implant clip 540 as described in detail above in reference to FIGS. 6A and 6B and FIGS. 12A and 12B. As shown in the illustrated embodiment, the first identification tag 40*a* is configured to be secured to the second identification tag 40*b*. According to one embodiment, a projection 580*a* of the first identification tag 40*a* is configured to be inserted into a recess 582*b* of the second identification tag 40*b*, such that the first identification tag 40*a* is configured to be stacked on the second identification tag 40*b*. In another embodiment, a projection 580*b* of the second identification tag 40*b* is configured to be inserted into a recess 582*a* of the first identification tag 40*a*, such that the second identification tag 40*b* is configured to be stacked on the first identification tag 40*a*.

Referring to FIG. 14, the system 10 can include the medical device 18, for example the instrument 21. The system can include a housing 1030 configured to carry the instrument 21 when the instrument 21 is not in use, and the system can further include the identification tag 40 configured to be coupled to at least one of the instrument 21 and the housing 1030.

The identification tag 40, as shown, can include the RFID chip 80 and the electrical circuit 82. The system 10 can be configured such that the RFID chip 80 is carried by the instrument or by the housing 1030. The electrical circuit 82 is defined partially by the identification tag 40, partially by the instrument 21, and partially by the housing 1030. According to one embodiment, the identification tag 40 includes a first electrically conductive wire 1062 (referred to herein as first wire 1062) that at least partially defines the first attachment region 84 of the electrical circuit 82. As shown the first electrically conductive wire 1062 can be attached directly to the RFID chip 80 at the first RFID location 86. The identification tag 40 can further include a second electrically conductive wire 1064 (referred to herein as second wire 1064) that defines the second attachment region 88 of the electrical circuit 82. As shown the second electrically conductive wire 1064 can be attached directly to the RFID chip 80 at the second RFID location 90.

The first wire 1062 and the second wire 1064 can each be carried by the instrument 21, by the housing 1030, or by a combination of the instrument 21 and the housing 1030. As shown in the illustrated embodiment, the identification tag 40 can be carried by the instrument 21. When the instrument 21 is positioned within in the housing 1030 a metallic portion 1032 of the housing 1030 forms a part of the electrical circuit 82 such that the electrical circuit 82 is closed, and the RFID chip 80 defines the first state. The metallic portion 1032 may include one or more brackets 1034 configured to secure the instrument 21 within the housing 1030. When the instrument 21 is removed from the housing 1030, for example for use in a medical procedure, the electrical circuit 82 is open, and the RFID chip 80 defines a second state that is different than the first state.

According to another embodiment, the identification tag 40 can be carried by the housing 1030. When the instrument 21 is positioned within in the housing 1030 a metallic portion 1024 of the instrument 21 forms a part of the electrical circuit 82 such that the electrical circuit 82 is closed, and the RFID chip 80 defines the first state. When the instrument 21 is removed from the housing 1030, for example for use in a medical procedure, the electrical circuit 82 is open, and the RFID chip 80 defines a second state that is different than the first state.

The system 10 can be configured for use such that each time RFID chip 80 switches from the first state to the second state, for example when the instrument 21 is removed from the housing 1030 for use in a medical procedure, the change in state is recorded. A set of data can be created from the change in states of the RFID chip 80 throughout the life cycle of the instrument 21. The data can be used to determine, for example the frequency of use of the instrument 21. Based on the results of the data decisions can be made regarding the assembly of future systems 10. For example, if the data indicates infrequent use of the instrument 21, future systems 10 may be assembled without the inclusion of the instrument 21.

Referring to FIGS. 1 to 15, the medical device 18 of the system 10 of any of the embodiments as described above can include an implant 20' either in addition to or in replacement of the implant 20. The implant 20' can include an implant body 22' having a first portion 28 that is configured to be implanted within a patient, and a second portion 30 that is configured to be detached from the first portion 28. According to one embodiment, the second portion 30 is not configured to be permanently implanted within a patient.

Referring to FIG. 15 the system 10 can include the medical device 18, for example the implant 20', and the identification tag 40 configured to be coupled to the implant 20'. According to one embodiment, the implant body 22' of the implant 20' can be in the form of a suture 520, as shown. The identification tag 40 includes the substrate 42 and the substrate 42 can include a package 640.

According to one embodiment, the suture 520 includes an suture body 522 having a first portion 524 that is configured to be implanted within a patient, and a second portion 526 that is configured to be detached from the first portion 524. As shown, the suture body 522 can include a suture thread 528 and a needle 530.

The identification tag 40, as shown, can include the RFID chip 80 and the electrical circuit 82 as described in detail in any of the embodiments above. The RFID chip 80 can be configured to be carried by the package 640 and the electrical circuit 82 is defined partially by the identification tag 40 and partially by the implant 20'. As shown, the suture 520 includes a metallic portion 532, for example defined by the needle 530, which forms a portion of the electrical circuit 82.

When the system 10 is in the first configuration, as shown in the illustrated embodiment, the identification tag 40 is coupled to the implant 20', the electrical circuit 82 is closed, and the RFID chip 80 defines the first state. When the system 10 is in the second configuration the identification tag 40 is decoupled from the implant 20', the electrical circuit 82 is open, and the RFID chip 80 defines a second state that is different than the first state. For example, removing the suture 520 from the package 640 removes the metallic portion 532 of the needle 530 from the electrical circuit 82 which opens electrical circuit 82.

Referring to FIGS. 1 to 16, the medical device 18 of the system 10 of any of the embodiments as described above can include an implant 20" either in addition to or in replacement of the implant 20 or 20'. The implant 20" can include an implant body 22". According to one embodiment, an entirety of the implant body 22" is configured to be removed from a patient prior to the conclusion of a surgery in which the implant 20" is used.

Referring to FIG. 16 the system 10 can include the medical device 18, for example the implant 20", and the identification tag 40 configured to be coupled to the implant 20". According to one embodiment, the implant body 22" of the implant 20" can be in the form of an instrument, for example a drill bit 620, as shown. The drill bit 620 is configured to drill a hole in a bone of a patient during a surgical procedure, and then be removed entirely from the patient prior to the conclusion of the surgical procedure. According to another embodiment, the implant body 22" of the implant 20" can be in the form of another surgical instrument, or medical device that is at least partially metallic. As shown, the identification tag 40 includes the substrate 42 and the substrate 42 can include structure similar to that of the spacer clamp 240 as described in detail above in reference to FIGS. 3 and 10A to 10C.

According to one embodiment, the drill bit 620 includes a drill bit body 622 having a first portion 624 that is configured to drill a hole in a bone of a patient, and a second portion 626 that is configured to be inserted into an instrument, for example a drill, to secure the drill bit 620 to the instrument. As shown, the first portion 624 can include a cutting flute 628.

The identification tag 40, as shown, can include the RFID chip 80 and the electrical circuit 82 as described in detail in any of the embodiments above. The RFID chip 80 can be configured to be carried by the identification tag 40 and the electrical circuit 82 is defined partially by the identification tag 40 and partially by the implant 20". As shown, the drill bit 620 includes a metallic portion 630, for example defined at least partially by the first portion 624, which forms a portion of the electrical circuit 82.

When the system 10 is in the first configuration, as shown in the illustrated embodiment, the identification tag 40 is coupled to the implant 20", the electrical circuit 82 is closed, and the RFID chip 80 defines the first state. When the system 10 is in the second configuration the identification tag 40 is decoupled from the implant 20", the electrical circuit 82 is open, and the RFID chip 80 defines a second state that is different than the first state. For example, removing the drill bit 620 from the identification tag 40 removes the metallic portion 630 of the drill bit 620 from the electrical circuit 82 which opens electrical circuit 82. According to one embodiment, after the system 10 is in the second configuration, the implant 20", as shown the drill bit 620, is configured to be coupled again to the identification tag 40, such that the system is in the first configuration. In the first configuration for the second time, the RFID chip 80 can define a third state that is different than both the first state and the second state. The RFID chip 80 can further define additional states each time the implant 20" is coupled to or decoupled from the identification tag 40. The current state of the RFID chip 80 can signify the number of uses of the implant 20", for example each time the implant 20" is coupled to the identification tag 40 signifies a use of the implant 20". Thus, according to one embodiment, the first state signifies zero uses, the third state signifies one use, the fifth state signifies two uses, etc. In addition, each of the states in which the implant 20" is decoupled from the identification tag 40 can signify that the implant 20" is in use. Thus, the second state, the fourth state, and the sixth state, etc. for example, can each signify that the implant 20" is in use.

The ability of the system 10 to track and transmit and/or store the number of uses can assist in determining how far the implant 20" is in its life cycle. For example the system 10 could contain the maximum number of uses in the life span of the drill bit 620, and once the state of the RFID chip 80 signifies that the number of uses of the drill bit 620 approaches or equals that maximum number of uses, the system 10 can be configured to notify the user, manufacturer, and/or supplier of the drill bit 620 that a replacement implant 20", for example the drill bit 620, is needed.

According to one embodiment, the substrate 42 can be configured to be secured to a case or another identification tag 40 so that the system 10 can be provided as part of a kit. Accordingly, the substrate 42 can include an engagement member 256 that is configured to secure the substrate 42 to a case or another identification tag 40. As shown in the illustrated embodiment, the engagement member 256 of the substrate 42 includes a projection 258 configured to be inserted into a corresponding recess in a case or another identification tag 40. Alternatively, the engagement member 256 of the substrate 42 can include a recess configured to receive a corresponding projection in a case. Alternatively, the substrate 42 can include a plurality of engagement members 256 or a plurality of recesses each configured to receive a corresponding projection in the case.

Referring to FIGS. 9A to 16, the embodiments of the system 10 are illustrated as including (and have been described as including) one RFID chip 80. In an alternate embodiment of any of the systems 10 illustrated in FIGS. 8A to 12B, the system 10 includes a plurality of RFID chips 80. For example, the system 10 illustrated in FIG. 11C could include a separate RFID chip 80 for each of the electrical circuits 82. Thus, the system 10 could include a first RFID chip 80a attached to the first electrical circuit 82a, a second RFID chip 80b attached to the second electrical circuit 82b, and so on.

Referring to FIG. 16, the system 10 can further include an enclosure 600 configured to carry the medical device 18, for example the implant 20, and the identification tag 40. The enclosure 600 includes an enclosure body 602 and a sterile interior 604 defined by the enclosure body 602. The enclosure 600 can be configured such that the size of the sterile interior 604 is sufficient to carry any of the embodiments of the implant 20 and the identification tag 40 entirely within the sterile interior 604. According to one embodiment, the size of the sterile interior 604 is also sufficient to carry any of the embodiments of the RFID chip 80 entirely within the sterile interior 604. In one embodiment, the system 10 includes the implant 20 coupled to the identification tag 40 within the sterile interior 604. The enclosure 600 can further include an RFID chip 606 as shown. The RFID chip 606 can define a first state when the enclosure 600 is intact, such that the sterile interior 604 is sealed. The RFID chip 606 can define a second state different than the first state when the enclosure 600 is ruptured, such that the sterile interior 604 is open to the environment outside the enclosure 600.

Referring to FIGS. 1 to 17, a method of assembling the system 10 is provided. The method including the step of coupling the identification tag 40 to the implant 20 such that the first attachment region 84 of the electrical circuit 82 of the identification tag 40 is attached to an RFID chip 80 of the identification tag 40 at a first RFID location 86 on the RFID chip, and a second attachment region 88 of the electrical circuit 82 is attached to the RFID chip 80 at a second RFID location 90 on the RFID chip 80 that is spaced from the first RFID location 86. The method further includes the step of placing the coupled implant 20 and the identification tag 40 into the sterile interior 604 of an enclosure 600.

According to one embodiment, the method can include inserting the implant 20 into a recess of the substrate 42, for example the through hole 348, such that the implant 20 defines a portion of the electrical circuit 82. According to one embodiment, the method can include moving the implant 20 into contact with the third attachment region 98 of the electrical circuit 82 that is positioned between the first attachment region 84 and the second attachment region 88, and further moving the implant 20 into contact with the fourth attachment region 100 of the electrical circuit 82, the fourth attachment region 100 positioned between the third attachment region 98 and the second attachment region 88. According to one embodiment, the method can include rotating the implant 20 about an axis, for example the sleeve axis 350, with respect to the substrate 42. According to one embodiment, the method can include translating the implant 20 along an axis, for example the sleeve axis 350, with respect to the substrate 42. According to one embodiment, the method can include inserting a portion of the implant 20 into a first area 164 having an outer perimeter defined by the attachment member 60, for example the wire 160, of the identification tag 40.

Referring still to FIGS. 1 to 17, a method of implanting an implant, for example the implant 20, is provided. The method including the step of selecting the system 10 that is in a first configuration such that the identification tag 40 of the system 10 is coupled to the implant 20 of the system 10, an electrical circuit 82 of the identification tag 40 is closed, and the RFID chip 80 of the system 10 defines a first state. The method can further include decoupling the identification tag 40 from the implant 20 such that the system 10 is in a second configuration in which the electrical circuit 82 is open and the RFID chip 80 defines a second state that is different than the first state. The method can further include implanting the decoupled implant 20 into a location within a patient's body. The method can further include placing the decoupled identification tag 40 in a location outside of the patient's body.

According to one embodiment, the method can include removing the implant 20 from a recess, for example the through hole 348, of the substrate 42 of the system 10. According to one embodiment, the method can include moving the implant 20 out of contact with a third attachment region 98 of the electrical circuit 82 that is positioned between the first attachment region 84 and the second attachment region 88, and moving the implant 20 out of contact with a fourth attachment region 100 of the electrical circuit 82, the fourth attachment region 100 positioned between the third attachment region 98 and the second attachment region 88. According to one embodiment, the method can include rotating the implant 20 about an axis, for example the sleeve axis 350, with respect to the substrate 42. According to one embodiment, the method can include translating the implant 20 along an axis, for example the sleeve axis 350, with respect to the substrate 42. According to one embodiment, the method can include removing a portion of the implant 20 from the first area 164 having an outer perimeter defined by, the attachment member 60, for example the wire 160, of the identification tag 40.

Figure 18A:
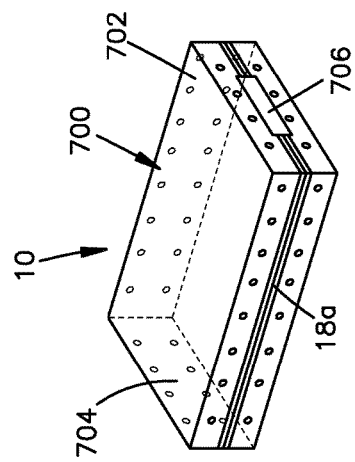
FIG. 18A is a perspective view of a system according to another embodiment, the system including an implant carrier having an RFID chip.
Figure 18B:
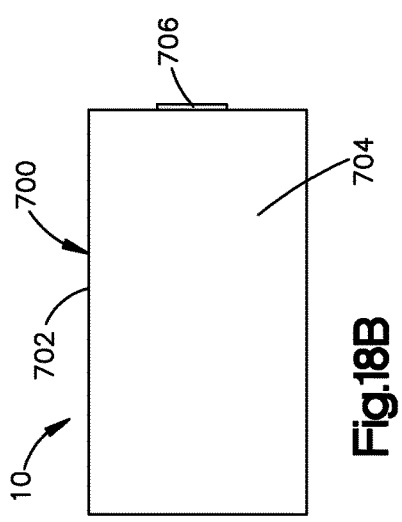
FIG. 18B is top plan view of the implant carrier illustrated in FIG. 18A.

Referring to FIGS. 18A and 18B, the system 10, according to one embodiment, can include an implant carrier, for example a case 700 configured to carry one or more of the implants 20 and the identification tags 40 as described in any of the embodiments above. The case 700 includes a case body 702 and an interior area 704 defined by the case body 702. The case 700 can further include an RFID chip 706, for example carried by the case body 702. The RFID chip 706 can define a first state when one of the one or more implants 20 and coupled identification tag 40 are positioned within the interior area 704. The RFID chip 706 can further define a second state when one of the one or more implants 20 is removed from the interior area 704.

Figure 19:
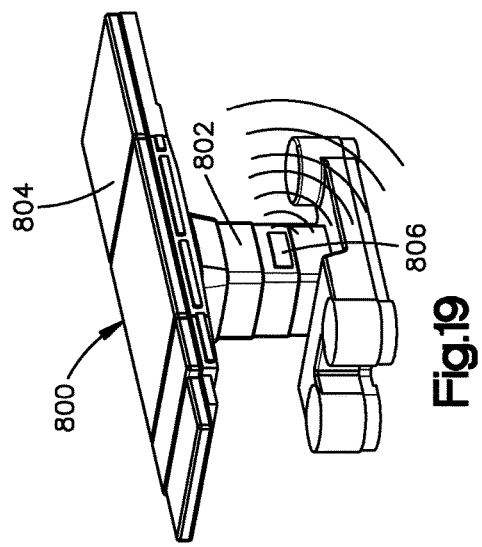
FIG. 19 is a perspective view of a system according to another embodiment, the system including a table having an RFID chip.

Referring to FIG. 19, the system 10, according to one embodiment, can include a table 800 configured to carry, according to one embodiment one or more of the implants 20 and the identification tags 40 as described in any of the embodiments above. According to another embodiment, the table 800 is configured to carry one or more of the case 700. The table 800 includes a table body 802 and a first area 804 defined at least partially by the table body 802. The table 800 can further include an RFID chip 806, for example carried by the table body 802. The RFID chip 806 can define a first state when one of the one or more implants 20 (or case 700) and coupled identification tag 40 are positioned within the first area 804. The RFID chip 806 can further define a second state when the one of the one or more implants 20 (or case 700) is removed from the first area 804.

Figure 20A:
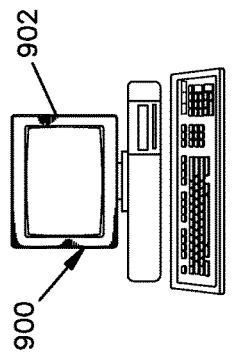
FIG. 20A is a perspective view of a system according to another embodiment, the system including a data storage medium.
Figure 20B:
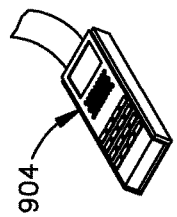
FIG. 20B is a perspective view of a system according to another embodiment, the system including a label printer.
Figure 20C:
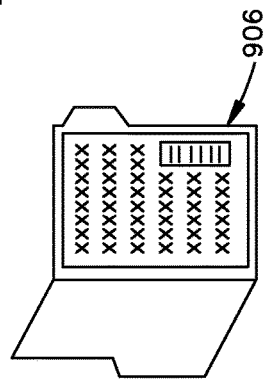
FIG. 20C is a perspective view of a system according to another embodiment, the system including a file.

Referring to FIGS. 20A to 20C, the system 10, according to one embodiment, can include any one of, or a combination of, a data storage medium 900 such as a computer 902, a label printer 904, and a file 906. The data storage medium 900 can be configured such that upon a change in the state of any of the RFID chips 80, 606, 706, 806 described herein, the change in state is recorded and stored on the data storage medium 900. The label printer 904 can be configured such that upon a change in state of any of the RFID chips 80, 606, 706, 806 described herein, the change in state is reflected in a printed medium, such as on a label that can be stored in a file 906, for example the file 906 of a patient who has had the implant 20 implanted during a surgery.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the claims.

What is claimed:

1. A medical device identification system comprising:
    a medical device; and
    an identification tag coupled to the medical device, the identification tag including an RFID chip and an electrical circuit, the electrical circuit including at least one electrically conductive wire defining a first attachment region attached to the RFID chip at a first RFID location, and the at least one electrically conductive wire further defining a second attachment region, a third attachment region, and a fourth attachment region, the second attachment region attached to the RFID chip at a second RFID location that is spaced from the first RFID location, the electrical circuit defining a path between the first attachment region and the second attachment region, the third attachment region positioned on the path between the first attachment region and the second attachment region, and the fourth attachment region positioned on the path between the third attachment region and the second attachment region;
    wherein 1) the system defines a first configuration in which the first attachment region is in electrical communication with the second attachment region along the electrical circuit, and a second configuration in which the first attachment region is electrically isolated from the second attachment region along the electrical circuit, 2) the RFID chip is in a first state when the system is in the first configuration, and the RFID chip is in a second state different than the first state when the system is in the second configuration, and 3) when the system is in the first configuration the third attachment region and the fourth attachment region are each attached to the medical device, and when the system is in the second configuration the third attachment region and the fourth attachment region are separated by a gap such that the third and fourth attachment regions are electrically isolated from one another.

2. The system of claim 1, wherein the medical device includes at least one of: 1) an implant configured to be implanted in a human body; and 2) an instrument configured for use in a medical procedure.

3. The system claim 1, wherein the electrical circuit is coupled to the medical device such that decoupling of the identification tag from the medical device causes a break in the electrical circuit at a location between the first attachment region and the second attachment region such that the electrical circuit is open.

4. The system of claim 1, wherein the RFID chip is an active chip that emits a radio frequency signal when the electrical circuit is closed, the identification tag includes an antenna configured to transmit the radio-frequency signal, the radio-frequency signal includes information that indicates whether the RFID chip is in the first state or the second state, and the electrically conductive wire defines at least a portion of the antenna.

5. The system of claim 1, wherein the RFID chip is an active chip that emits a radio frequency signal when the electrical circuit is open, the identification tag includes an antenna configured to transmit the radio-frequency signal, the radio-frequency signal includes information that indicates whether the RFID chip is in the first state or the second state, and the electrically conductive wire defines at least a portion of the antenna.

6. The system of claim 5, wherein the medical device defines a portion of the electrical circuit.

7. A method of assembling a medical device identification system, the method comprising the steps of:
    coupling an identification tag to a medical device such that 1) a first attachment region of an electrical circuit of the identification tag that is attached to an RFID chip of the identification tag at a first RFID location on the RFID chip is in electrical communication with a second attachment region of the electrical circuit of the identification tag that is attached to the RFID chip at a second RFID location on the RFID chip that is spaced from the first location and 2) the system is in a first configuration in which the RFID chip is in a first state;
    the coupling step including the step of inserting the medical device into a recess of a substrate such that the medical device defines a portion of the electrical circuit;
    the inserting step includes the step of moving the medical device into contact with both 1) a third attachment region of the electrical circuit that is positioned between the first attachment region and the second attachment region and 2) a fourth attachment region of the electrical circuit that is positioned between the third attachment region and the second attachment region; and
    placing the coupled medical device and identification tag into an interior of an enclosure,
    wherein the system defines a second configuration in which 1) the first attachment region is electrically isolated from the second attachment region along the electrical circuit and 2) the RFID chip is in a second state different than the first state.

8. The method of claim 7, wherein the medical device includes an implant configured to be inserted into a human body, and the interior of the enclosure is a sterile interior.

9. The method of claim 8, wherein the moving step includes at least one of: 1) rotating the medical device about an axis with respect to the substrate, and 2) translating the medical device along an axis with respect to the substrate.

10. A method of implanting an implant, the method comprising the steps of:
    selecting an implant for implantation into a patient, wherein the implant is coupled to an identification tag that includes an RFID chip and an electrical circuit, the electrical circuit including at least one electrically conductive wire, the at least one electrically conductive wire defining a first attachment region attached to the RFID chip at a first RFID location, and the at least one electrically conductive wire defining a second attachment region attached to the RFID chip at a second RFID location spaced from the first RFID location, wherein the first attachment region is in electrical communication with the second attachment region along the electrical circuit, and the RFID chip is in a first state;

decoupling the identification tag from the implant so as to cause a break in the electrical circuit, thereby electrically isolating the first attachment region from the second attachment region along the circuit;

the decoupling step including the step of removing the implant from a recess of a substrate of the system;

the removing step includes moving the implant out of contact with both 1) a third attachment region of the electrical circuit that is positioned between the first attachment region and the second attachment region and 2) a fourth attachment region of the electrical circuit that is positioned between the third attachment region and the second attachment region;

in response to the decoupling step, causing the RFID chip to define a second state that is different than the first state;

implanting the decoupled implant into the patient; and sensing the second state of the RFID chip.

11. The method of claim 10, wherein the moving step includes rotating the implant about an axis with respect to the substrate.

12. The method of claim 10, wherein the moving step includes translating the implant along an axis with respect to the substrate.

13. The method of claim 10, wherein the decoupling step includes removing a portion of the implant from a first area having an outer perimeter defined by the at least one electrically conductive wire.

14. The method of claim 10, further comprising the steps of:

transmitting the second state of the RFID chip;

storing the second state of the RFID chip; and associating the second state of the RFID chip with the patient, wherein the associating step includes recording the state of the RFID chip in a file associated with the patient.

* * * * *